United States Patent [19]
Gilg et al.

[11] Patent Number: 5,602,196
[45] Date of Patent: Feb. 11, 1997

[54] BISPHENOL ESTER DERIVATIVES

[75] Inventors: Bernard Gilg, Louis-La-Chaussée, France; Rita Pitteloud, Praroman, Switzerland

[73] Assignee: Ciba-Geigy Corporation, Tarrytown, N.Y.

[21] Appl. No.: 562,774

[22] Filed: Nov. 27, 1995

[30] Foreign Application Priority Data

Dec. 5, 1994 [CH] Switzerland .................. 3684/94

[51] Int. Cl.$^6$ .............................. C08K 5/41; C07C 69/76
[52] U.S. Cl. .................. 524/171; 524/335; 524/336; 544/171; 548/268.2; 548/261; 548/165; 548/341.5; 549/501; 546/239; 558/398; 560/61; 560/140; 560/125; 560/126
[58] Field of Search .................. 560/61, 140, 125, 560/126; 546/239; 544/171; 549/501; 548/268.2, 341.5, 261, 165; 558/398; 524/335, 336, 171

[56] References Cited

U.S. PATENT DOCUMENTS

| | | | |
|---|---|---|---|
| 4,107,137 | 8/1978 | Pronx et al. ................. | 260/45.85 |
| 4,311,637 | 1/1982 | Cottman ..................... | 260/45.85 |
| 4,414,408 | 11/1983 | Cottman ..................... | 560/144 |
| 5,128,398 | 7/1992 | Sasaki et al. ................ | 524/291 |

FOREIGN PATENT DOCUMENTS

| | | |
|---|---|---|
| 0479560 | 4/1992 | European Pat. Off. . |
| 3718751 | 1/1988 | Germany . |
| 4308581 | 10/1992 | Japan . |

OTHER PUBLICATIONS

Patent Abstract of Japan, vol, 8, No. 15, Jan. 1984.
Patent Abstract of Japan, vol. 7, No. 195, Aug. 1983.
Derwent Abstract 88-008082/02 of De 3,718,751.
Ed. D. Neville Jones, Comprehensive Organic Chemistry, vol. 3, pp. 124–126, 174, Pergamon Press (1979).
G. P. Dado & S. H. Gellman, J. Am. Chem. Soc., vol. 116, pp. 1054–1062, (1994).
R. V. Christian, Jr. & R. M. Hixon, J.A.C.S., vol. 70, p. 1333, (1948).
Wiley et al., J.A.S.C., vol. 76, p. 4933, (1954).

*Primary Examiner*—Joseph Conrad, III
*Attorney, Agent, or Firm*—Michele A. Kovaleski; Luther A. R. Hall

[57] ABSTRACT

Stabilisers of formula I

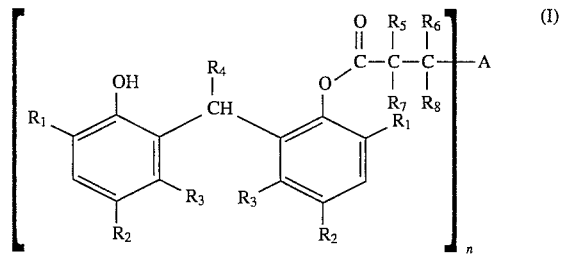

wherein $R_1$ and $R_2$ may be $C_1$–$C_5$alkyl, the substituents $R_3$ to $R_8$ may be hydrogen, the variable n may be 1 or 2, and, when n is 1, A may be an alkoxy radical, and, when n is 2, A may be a diamine radical.

16 Claims, No Drawings

BISPHENOL ESTER DERIVATIVES

The present invention relates to novel bisphenol derivatives, to the use thereof and to the organic material stabilised therewith against oxidative, thermal and light-induced degradation.

The use of some bisphenol ester derivatives as stabilisers is disclosed, inter alia, in JP-A-Hei 4-308 581, DE-A-3 718 751, EP-A-479 550 and U.S. Pat. No. 4,414,408.

In one of its aspects, the invention relates to compounds of formula I

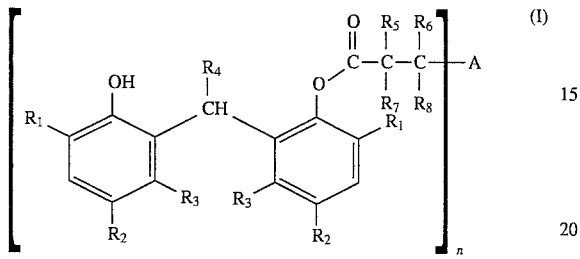

wherein
the substituents $R_1$ are each independently of one another $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl, $C_7$–$C_9$phenylalkyl or —$CH_2$—S—$X_1$, the substituents $R_2$ are each independently of one another hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl, $C_7$–$C_9$phenylalkyl, —$CH_2$—S—$X_1$, —$(CH_2)_p COO$—$X_2$ or —$(CH_2)_q O$—$X_3$, the substituents $R_3$ are each independently of one another hydrogen or $C_1$–$C_4$alkyl, $R_4$ is hydrogen or $C_1$–$C_8$alkyl, $R_5$ is hydrogen, $C_1$–$C_{10}$alkyl, phenyl, —$CH_2$—COO—$X_4$ or CN, $R_6$ is hydrogen, $C_1$–$C_4$alkyl, phenyl, —COO—$X_5$, —CN or —CON($X_6$)($X_7$), $R_7$ is hydrogen or $C_1$–$C_{10}$alkyl, $R_8$ is hydrogen, $C_1$–$C_4$alkyl or phenyl, $X_1$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or —$(CH_2)_r COO$—$Y_1$, $X_2$, $X_4$ and $X_5$ are each independently of one another $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, $X_3$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl, $C_1$–$C_{25}$alkanoyl, $C_3$–$C_{25}$alkenoyl, $C_3$–$C_{25}$alkanoyl which is interrupted by oxygen, sulfur or >N—$Y_2$, $C_6$–$C_9$cycloalkylcarbonyl, benzoyl, $C_1$–$C_4$alkyl-substituted benzoyl, thenoyl or furoyl, $X_6$ and $X_7$ are each independently of the other hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl or $C_7$–$C_9$phenylalkyl, $Y_1$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, $Y_2$ is hydrogen or $C_1$–$C_8$alkyl, p is 0, 1 or 2, q is an integer from 0 to 8, r is 1 or 2, n is an integer from 1 to 4, and, when n is 1, A is a group —O—$Z_1$, —N($Z_2$)($Z_3$), —NH(O$Z_4$), —O—N=C($Z_5$)($Z_6$), —S(O)$_m Z_7$, —NH—$Z_8$ or —S—$Z_8$, or A is also an unsubstituted or $C_1$–$C_4$alkyl-substituted heterocyclic radical which has the free valence at a nitrogen atom, $Z_1$ is hydrogen, $C_1$–$C_{25}$alkyl, $C_3$–$C_{25}$alkyl which is interrupted by oxygen, sulfur or >N—$Y_2$, $C_3$–$C_{24}$alkenyl, a monocyclic saturated hydrocarbon radical containing 5 to 20 carbon atoms, a bicyclic saturated hydrocarbon radical containing 7 to 20 carbon atoms, a tricyclic saturated hydrocarbon radical containing 10 to 20 carbon atoms, $C_5$–$C_{12}$cycloalkenyl, $C_1$–$C_4$alkyl-substituted $C_5$–$C_{12}$cycloalkenyl, $C_7$–$C_9$phenylalkyl, $C_7$–$C_9$phenylalkyl which is substituted at the phenyl ring by $C_1$–$C_4$alkyl; tetrahydrofurfuryl, tetrahydroabietyl, $C_1$–$C_{25}$alkanoyl, $C_3$–$C_{25}$alkenoyl, $C_3$–$C_{25}$alkanoyl which is interrupted by oxygen, sulfur or >N—$Y_2$, $C_6$–$C_9$cycloalkylcarbonyl, benzoyl, $C_1$–$C_4$alkyl-substituted benzoyl, thenoyl, furoyl or a group of formula IIa or IIb,

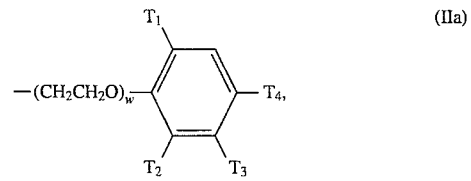

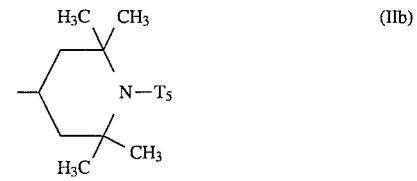

$Z_2$ is hydrogen, $C_1$–$C_{25}$alkyl, OH-substituted $C_2$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl, $C_1$–$C_{25}$alkanoyl, $C_3$–$C_{25}$alkenoyl, $C_3$–$C_{25}$alkanoyl which is interrupted by oxygen, sulfur or >N—$Y_2$, $C_6$–$C_9$cycloalkylcarbonyl, benzoyl, $C_1$–$C_4$alkyl-substituted benzoyl, thenoyl, furoyl, —$(CH_2)_p COO$—$X_2$ or a radical of formula IIb, $Z_3$ is hydrogen, $C_1$–$C_{25}$alkyl, OH-substituted $C_2$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or a group of formula IIb, or $Z_2$ and $Z_3$, taken together, are $C_3$–$C_6$alkylene, $C_3$–$C_6$xoalkylene or $C_3$–$C_6$alkylene which is interrupted by oxygen, sulfur or >N—$T_6$, $Z_4$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, $Z_5$ and $Z_6$ are each independently of the other hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5C_{12}$cycloalkenyl, phenyl, $C_1$–$C_4$alkyl-substituted phenyl or $C_7$–$C_9$phenylalkyl, or $Z_5$ and $Z_6$, together with the linking carbon atom, form an unsubstituted or a $C_1$–$C_4$alkyl-substituted $C_5$–$C_{12}$cycloalkylidene ring, $Z_7$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or —$(CH_2)_r$COO—$Y_1$, $Z_8$ is unsubstituted or $C_1$–$C_4$alkyl-substituted 2-benzoxazolyl or unsubstituted or $C_1$–$C_4$alkyl-substituted 2-benzothiazolyl, $T_1$ and $T_2$ are each independently of the other hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl, $C_7$–$C_9$phenylalkyl or —$CH_2$—$S$—$X_1$, $T_3$ is hydrogen or $C_1$–$C_4$alkyl, $T_4$ is hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl, $C_7$–$C_9$phenylalkyl, —$CH_2$—$S$—$X_1$, —$(CH_2)_p$COO—$X_2$ or —$(CH_2)_q$O—$X_3$, $T_5$ is hydrogen, $C_1$–$C_8$alkyl, —OH-substituted $C_2$–$C_4$alkyl, O·, —OH, —NO, —$CH_2$CN, $C_1$–$C_{18}$alkoxy, $C_5$–$C_{12}$cycloalkoxy, $C_3$–$C_6$alkenyl, $C_7$–$C_9$phenylalkyl, $C_7$–$C_9$phenylalkyl which is substituted at the phenyl ring by $C_1$–$C_4$alkyl; $C_1$–$C_8$alkanoyl, $C_3$–$C_8$alkenoyl or benzoyl, $T_6$ is $C_1$–$C_{12}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, m is 1 or 2, w is 0 or 1, when n is 2, A is a group of formula IIIa, IIIb, IIIc, IIId, IIIe or IIIf,

  (IIIa)

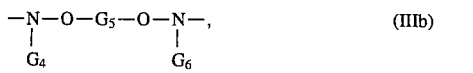  (IIIb)

  (IIIc)

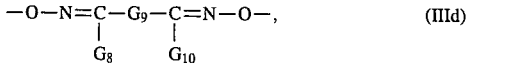  (IIId)

  (IIIe)

  (IIIf)

$G_1$ and $G_3$ are each independently of the other hydrogen, $C_1$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl, —$(CH_2)_p$COO—$X_2$ or a radical of formula IIb, $G_2$ is $C_2$–$C_{12}$alkylene, $C_4$–$C_{20}$alkylene which is interrupted by oxygen, sulfur or >N—$Y_2$, $C_4$–$C_{20}$alkenylene, $C_4$–$C_{20}$alkynylene, ($C_1$–$C_4$alkylene)-phenylene-($C_1$–$C_4$alkylene), a monocyclic saturated hydrocarbon radical with two free valences and containing 5 to 12 carbon atoms, a bicyclic saturated hydrocarbon radical with two free valences and containing 7 to 30 carbon atoms, phenylene, $C_1$–$C_4$alkyl-substituted phenylene, naphthylene, $C_2$–$C_{20}$alkanedioyl, $C_4$–$C_{20}$alkenedioyl or carboxybenzoyl, $G_4$ and $G_6$ are each independently of the other hydrogen, $C_1$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or a group of formula IIb, $G_5$ is $C_2$–$C_{12}$alkylene, $C_4$–$C_{20}$alkylene which is interrupted by oxygen, sulfur or >N—$Y_2$, $C_4$–$C_{20}$alkenylene, $C_4$–$C_{20}$alkynylene, ($C_1$–$C_4$alkylene)-phenylene-($C_1$–$C_4$alkylene), a monocyclic saturated hydrocarbon radical with two free valences and containing 5 to 12 carbon atoms, a bicyclic saturated hydrocarbon radical with two free valences and containing 7 to 30 carbon atoms, phenylene, $C_1$–$C_4$alkyl-substituted phenylene or naphthylene, $G_7$ is $C_2$–$C_{20}$alkylene, $C_4$–$C_{20}$alkylene which is interrupted by oxygen, sulfur or >N—$Y_2$, $C_4$–$C_{20}$alkenylene, $C_4$–$C_{20}$alkynylene, ($C_1$–$C_4$alkylene)-phenylene-($C_1$–$C_4$alkylene ), a monocyclic saturated hydrocarbon radical with two free valences and containing 5 to 12 carbon atoms, a bicyclic saturated hydrocarbon radical with two free valences and containing 7 to 30 carbon atoms, phenylene, $C_1$–$C_4$alkyl-substituted phenylene or naphthylene, $C_2$–$C_{20}$alkanedioyl, $C_4$–$C_{20}$alkenedioyl, carboxybenzoyl or a group of formula IVa, IVb or IVc

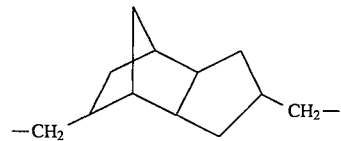  (IVa)

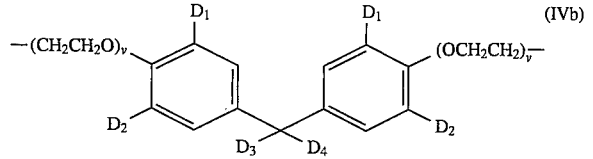  (IVb)

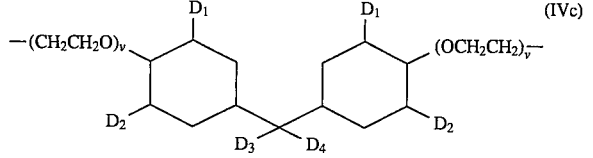  (IVc)

$G_8$ and $G_{10}$ are each independently of the other hydrogen, $C_1$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or a group of formula IIb, $G_9$ and $G_{11}$ are $C_2$–$C_{12}$alkylene, $C_4$–$C_{20}$alkylene which is interrupted by oxygen, sulfur or >N—$Y_2$, $C_4$–$C_{20}$alkenylene, $C_4$–$C_{20}$alkynylene, ($C_1$–$C_4$alkylene)-phenylene-($C_1$–$C_4$alkylene), a monocyclic saturated hydrocarbon radical with two free valences and containing 5 to 12 carbon atoms, a bicyclic saturated hydrocarbon radical with two free valences and containing 7 to 30 carbon atoms, phenylene, $C_1$–$C_4$alkyl-substituted phenylene or naphthylene, $G_{12}$ is hydrogen, $C_1$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or a group of formula IIb, the substituents $D_1$ are each independently of the other hydrogen, $C_1$–$C_8$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, the substituents $D_2$ are each independently of the other hydrogen, $C_1$–$C_8$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, $D_3$ and $D_4$ are each independently of the other hydrogen, $CF_3$, $C_1$–$C_{12}$alkyl or phenyl, or $D_3$ and $D_4$, together with the linking carbon atom, form an unsubstituted or $C_1$–$C_4$alkyl-substituted $C_5$–$C_{12}$cycloalkylidene ring, t is 1 or 2, v is 0 or 1, when n is 3, A is a group of formula Va, Vb or Vc,

(Va)

(Vb)

(Vc)

$E_1$ is $C_3$–$C_7$alkanetriyl, $E_2$ and $E_3$ are $C_2$–$C_8$alkylene, when n is 4, A is a group of formula VI

(VI)

and $E_4$ is $C_4$–$C_{10}$alkanetetrayl or $C_4$–$C_{10}$alkanetetrayl which is interrupted by oxygen.

Alkyl containing up to 25, preferably up to 18 and most preferably up to 10, carbon atoms, is typically methyl, ethyl, propyl, isopropyl, n-butyl, sec-butyl, isobutyl, tert-butyl, 2-ethylbutyl, n-pentyl, tert-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methyl-heptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl.

One of the preferred meanings of $R_1$ and $R_2$ is branched $C_1$–$C_{10}$alkyl, more particularly $C_1$–$C_5$alkyl, typically methyl, tert-butyl and tert-pentyl.

One of the preferred meanings of $R_4$ is $C_1$–$C_4$alkyl, more particularly methyl.

One of the preferred meanings of $Y_2$ is $C_1$–$C_4$alkyl, more particularly methyl.

One of the preferred meanings of $Z_1$ and $Z_2$ is $C_1$–$C_{18}$alkyl.

One of the preferred meanings of $Z_7$ is $C_1$–$C_{18}$alkyl, more particularly $C_1$–$C_{10}$alkyl.

One of the preferred meanings of $T_1$, $T_2$ and $T_4$ is $C_1$–$C_4$alkyl, more particularly methyl and tert-butyl.

One of the preferred meanings of $T_5$ is $C_1$–$C_4$alkyl, more particularly methyl.

One of the preferred meanings of $T_6$ is $C_1$–$C_4$alkyl.

Illustrative examples of $C_3$–$C_{25}$alkyl which is interrupted by oxygen, sulfur or >N—$Y_2$ are $CH_3$—O—$CH_2CH_2$—, $CH_3$—$CH_2$—O—$CH_2$—$CH_2$—$CH_2$—O—, $(CH_3)_2CH$—O—$CH_2$—$CH_2$—, $CH_3$—S—$CH_2CH_2$—, $CH_3$—NH—$CH_2CH_2$—, $CH_3$—N($CH_3$)—$CH_2CH_2$—, $CH_3$—O—$CH_2CH_2$—O—$CH_2CH_2$—, $CH_3$—(O—$CH_2CH_2$—)$_2$O—$CH_2CH_2$—, $CH_3$—(O—$CH_2CH_2$—)$_3$O—$CH_2CH_2$— and $CH_3$—(O—$CH_2CH_2$—)$_4$O—$CH_2CH_2$—. $C_3$–$C_{25}$Alkyl which is interrupted by oxygen or >N-$Y_2$ is preferred, and $C_3$–$C_{10}$alkyl which is interrupted by oxygen is more preferred. The radicals ($C_1$–$C_5$alkyl)—(OCH$_2$CH$_2$)$_{1-10}$— and ($C_1$–$C_5$alkyl)—(OCH$_2$CH$_2$)$_{1-2}$— are particularly preferred.

—OH-substituted $C_2$–$C_{25}$alkyl, in particular —OH-substituted $C_2$–$C_4$alkyl, may typically be 2-hydroxyethyl, 2-hydroxypropyl, 2-hydroxybutyl or 4-hydroxybutyl.

$C_1$–$C_{18}$Alkoxy is typically methoxy, ethoxy, propoxy, isopropoxy, butoxy, isobutoxy, pentyloxy, isopentyloxy, hexyloxy, heptyloxy, octyloxy, decyloxy, dodecyloxy, tetradecyloxy, hexadecyloxy and octadecyloxy. $C_6$–$C_{12}$Alkoxy, in particular heptyloxy and octyloxy, is preferred.

Alkenyl containing up to 24, preferably up to 18, carbon atoms, is typically vinyl, propenyl, isopropenyl, 2-butenyl, 3-butenyl, isobutenyl, 3-methyl-but-2-enyl, n-oct-2-enyl, n-dodec-2-enyl, isododecenyl, n-octadec-2-enyl or n-octadec-4-enyl. Alkenyl radicals in which the carbon atom in 1-position are saturated are preferred. $C_3$–$C_{18}$Alkenyl is particularly preferred.

Unsubstituted or $C_1$–$C_4$alkyl-substituted $C_5$–$C_{12}$cycloalkyl is typically cyclopentyl, cyclohexyl, cycloheptyl, cyclooctyl, cyclododecyl, 2- or 4-methylcyclohexyl, dimethylcyclohexyl, trimethylcyclohexyl or tert-butylcyclohexyl. Unsubstituted or $C_1$–$C_4$alkyl-substituted $C_5$–$C_8$-cycloalkyl, more particularly cyclohexyl, is preferred.

One of the preferred meanings of $R_1$ is cyclohexyl.

Illustrative examples of $C_5$–$C_{12}$cycloalkoxy are cyclopentyloxy, cyclohexyloxy, cycloheptyloxy, cyclooctyloxy, cyclodecyloxy and cyclododecyloxy. Cyclopentyloxy and cyclohexyloxy are preferred.

A monocyclic saturated hydrocarbon radical containing 5 to 20 carbon atoms is typically unsubstituted or $C_1$–$C_4$alkyl-substituted $C_5$–$C_{12}$cycloalkyl or ($C_5$–$C_{12}$cycloalkyl)—($C_1$–$C_4$alkyl) which is unsubstituted or substituted in the cycloalkyl moiety by $C_1$–$C_4$alkyl, typically cyclohexylmethyl, methylcyclohexylmethyl or dimethylcyclohexylmethyl.

A bicyclic saturated hydrocarbon radical containing 7 to 20 carbon atoms is typically

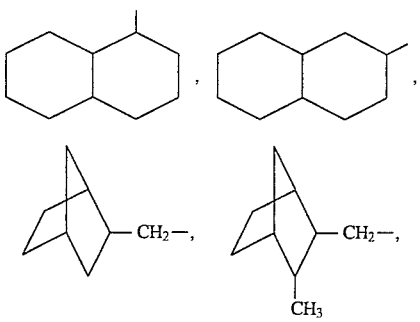

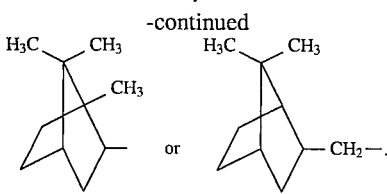

A tricyclic saturated hydrocarbon radical containing 10 to 20 carbon atoms is typically

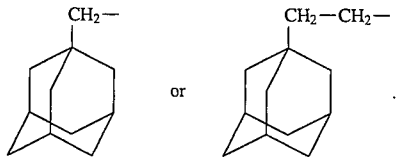

Typical examples of unsubstituted or $C_1$–$C_4$alkyl-substituted $C_5$–$C_{12}$cycloalkenyl, preferably $C_5$–$C_8$cycloalkenyl, are cyclohex-2-enyl, cyclohept-3-enyl and 4-tert-butylcyclohex-2-enyl. Cyclohexenyl is preferred.

$C_1$–$C_4$Alkyl-substituted phenyl is typically methylphenyl, dimethylphenyl, trimethylphenyl, ethylphenyl, diethylphenyl, isopropylphenyl, tert-butylphenyl, di-tert-butylphenyl or methyl-di-t-butylphenyl.

Illustrative examples of an unsubstituted or $C_1$–$C_4$alkyl-substituted $C_5$–$C_{12}$cycloalkylidene ring are

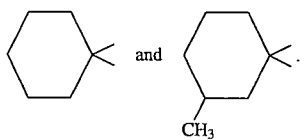

A $C_5$–$C_8$cycloalkylidene ring is preferred.

Illustrative examples of $C_7$–$C_9$phenylalkyl which may be unsubstituted or substituted at the phenyl ring by $C_1$–$C_4$alkyl are benzyl, phenethyl, 3-phenylpropyl, α-methylbenzyl, α,α-dimethylbenzyl, methylbenzyl, dimethylbenzyl, trimethylbenzyl and tert-butylbenzyl.

Alkanoyl containing up to 25 carbon atoms may be methanoyl, ethanoyl, propanoyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, octadecanoyl, nonadecanoyl or eicosanoyl. $C_1$–$C_{18}$Alkanoyl is a preferred meaning.

$C_3$–$C_{25}$Alkanoyl which is interrupted by oxygen, sulfur or >N—$Y_2$ will typically be —CO—$CH_2CH_2$—S—($C_1$–$C_{10}$alkyl), —CO—$CH_2CH_2$—O—($C_1$–$C_{10}$alkyl) and —CO—$CH_2CH_2$—N($Y_2$)—($C_1$–$C_{10}$alkyl).

$C_3$–$C_{25}$Alkanoyl which is interrupted by oxygen or >N—$Y_2$ is preferred.

$C_3$–$C_{25}$Alkenoyl is typically acryloyl, methacryloyl, crotonoyl, isocrotonoyl and oleolyl. $C_3$–$C_{18}$Alkenoyl is preferred.

$C_6$–$C_9$Cycloalkylcarbonyl is typically cyclopentylcarbonyl, cyclohexylcarbonyl, cycloheptylcarbonyl or cyclooctylcarbonyl.

$C_1$–$C_4$Alkyl-substituted benzoyl is typically methylbenzoyl or tert-butylbenzoyl.

Illustrative examples of an unsubstituted or $C_1$–$C_4$alkyl-substituted heterocyclic radical which has the free valency at a nitrogen atom are:

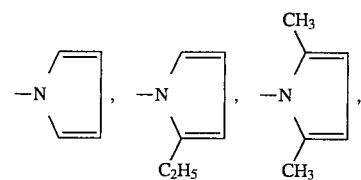

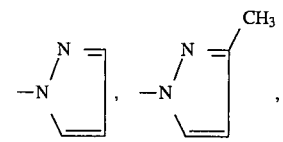

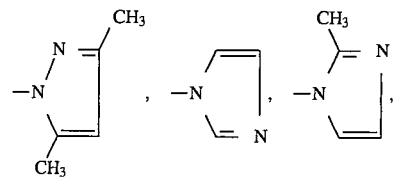

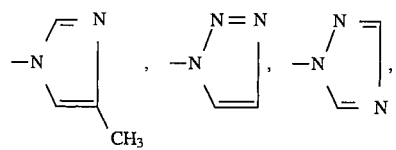

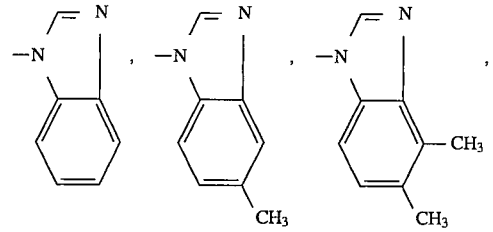

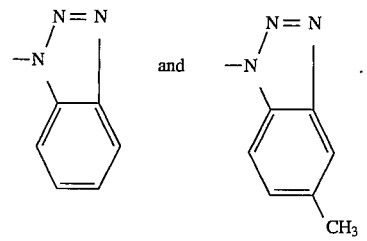

A 5–7-membered heteromonocyclic radical and a 9–10-membered heterobicyclic radical is preferred. The particularly preferred hetero atom is nitrogen. Also preferred are: unsubstituted or $C_1$–$C_4$alkyl-substituted 1-pyrrolyl, unsubstituted or $C_1$–$C_4$alkyl-substituted 1-pyrazolyl, unsubstituted or $C_1$–$C_4$alkyl-substituted 1-imidazolyl, 1-triazolyl, unsubstituted or $C_1$–$C_4$alkyl-substituted 1-benzimidazolyl or 1-benzotriazolyl.

$Z_8$ is typically a group

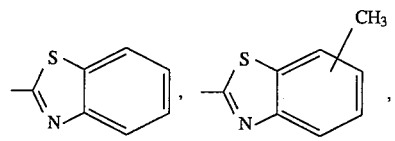

Alkylene containing up to 20, preferably up to 12 or up to 6, carbon atoms, is typically ethylene, propylene, trimethylene, tetramethylene, pentamethylene, 2,2-dimethyltrimethylene, hexamethylene, trimethylhexamethylene, octamethylene, decamethylene, undecamethylene or dodecamethylene.

One of the preferred meanings of $G_2$, $G_5$, $G_7$, $G_9$ and $G_{11}$ is $C_2$–$C_8$alkylene.

$C_4$–$C_{20}$Alkylene which is interrupted by oxygen, sulfur or $>$N—$Y_2$ is typically —CH$_2$CH$_2$—O—CH$_2$CH$_2$—, —CH$_2$CH$_2$—S—CH$_2$CH$_2$—, —CH$_2$CH$_2$—NH—CH$_2$CH$_2$—, —CH$_2$CH$_2$CH$_2$—NH—CH$_2$CH$_2$CH$_2$—, —CH$_2$CH$_2$CH$_2$—NH—CH$_2$CH$_2$—, —CH$_2$CH$_2$CH$_2$CH$_2$—NH—CH$_2$CH$_2$CH$_2$—, —(CH$_2$)$_6$—NH—(CH$_2$)$_6$—, —CH$_2$CH$_2$—N(CH$_3$)—CH$_2$CH$_2$—, —CH$_2$CH$_2$CH$_2$—N(CH$_3$)—CH$_2$CH$_2$CH$_2$—, —CH$_2$CH$_2$—(O—CH$_2$CH$_2$—)$_2$O—CH$_2$CH$_2$—, —CH$_2$CH$_2$—(O—CH$_2$CH$_2$—)$_3$O—CH$_2$CH$_2$—, —CH$_2$CH$_2$—(O—CH$_2$CH$_2$—)$_4$O—CH$_2$CH$_2$—, —CH$_2$CH$_2$CH$_2$CH$_2$—O—CH$_2$CH$_2$CH$_2$CH$_2$—O —CH$_2$CH$_2$CH$_2$CH$_2$—, —CH$_2$CH$_2$—NH—CH$_2$CH$_2$—NH—CH$_2$CH$_2$—, —CH$_2$CH$_2$CH$_2$—NH—CH$_2$CH$_2$—NH—CH$_2$CH$_2$CH$_2$— or —CH$_2$CH$_2$CH$_2$—NH—CH$_2$CH$_2$CH$_2$CH$_2$—NH—CH$_2$CH$_2$CH$_2$—. $C_4$–$C_{20}$Alkylene which is interrupted by oxygen or $>$N—$Y_2$ is preferred. The radicals —CH$_2$CH$_2$—O—CH$_2$CH$_2$— and —CH$_2$CH$_2$CH$_2$CH$_2$—O—CH$_2$CH$_2$CH$_2$CH$_2$—O—CH$_2$CH$_2$CH$_2$CH$_2$— are particularly preferred.

A preferred meaning of —N($Z_2$)($Z_3$) is morpholino.

$C_3$–$C_6$Alkylene which is interrupted by $>$N—$T_6$ is typically —CH$_2$CH$_2$—N(CH$_3$)—CH$_2$CH$_2$—, —CH$_2$CH$_2$CH$_2$—N(CH$_3$)—CH$_2$CH$_2$CH$_2$—.

$C_3$–$C_6$Oxoalkylene is typically —CO—CH$_2$CH$_2$CH$_2$CH$_2$—.

$C_4$–$C_{20}$Alkenylene is typically 2-but-1,4-enylene, 3-pent-1,5-enylene or 2-hex-1,6-enylene.

$C_4$–$C_{20}$Alkynylene is typically 2-butynylene (—CH$_2$—C≡C—CH$_2$—), 2-pentynylene, 2-hexynylene, 3-hexynylene, 3-heptynylene, 2-decynylene, 4-decynylene or 8-octadecynylene.

($C_1$–$C_4$Alkylene)phenylene-($C_1$–$C_4$alkylene) is typically a group

Illustrative examples of a monocyclic saturated hydrocarbon radical having two free valences and containing 5 to 12 carbon atoms are a group and $C_5$–$C_{12}$cycloalkylene such as cyclopentylene, cyclohexylene, cycloheptylene or cyclooctylene.

Illustrative examples of a bicyclic saturated hydrocarbon radical having two free valences and 7 to 30 carbon atoms are $C_1$–$C_4$Alkyl-substituted phenylene is typically methylphenylene or tert-butylphenylene.

$C_2$–$C_{20}$Alkanedioyl is typically ethanedioyl, propanedioyl, butanedioyl, pentanedioyl, hexanedioyl, heptanedioyl, octanedioyl, nonanedioyl or decanedioyl. $C_2$–$C_{10}$Alkanedioyl is preferred.

$C_4$–$C_{20}$Alkenedioyl is typically maleoyl, fumaroyl, citraconoyl or mesaconoyl.

Illustrative examples of $C_3$–$C_7$alkanetriyl are

Illustrative examples of $C_4$–$C_{10}$alkanetetrayl or $C_4$–$C_{10}$alkanetetrayl which is interrupted by oxygen are $R_5$, $R_6$, $R_7$ and $R_8$ are preferably hydrogen.

The variable n is preferably 1 or 2.

Preferred compounds of formula I are those, wherein the substituents $R_1$ are each independently of one another $C_1$–$C_{18}$alkyl, $C_2$–$C_{18}$alkenyl, $C_5$–$C_8$-cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl, $C_7$–$C_9$phenylalkyl or —CH$_2$—S—$X_1$, the substituents $R_2$ are each independently of one another hydrogen, $C_1$–$C_{18}$alkyl, $C_2$–$C_{18}$alkenyl, $C_5$–$C_8$-cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl, $C_7$–$C_9$phenylalkyl, —CH$_2$—S—$X_1$, —(CH$_2$)$_p$COO—$X_2$ or —(CH$_2$)$_q$O—$X_3$, the substituents $R_3$ are each independently of one another hydrogen or $C_1$–$C_4$alkyl, $R_4$ is hydrogen or $C_1$–$C_8$alkyl, $R_5$ is hydrogen, $C_1$–$C_{10}$alkyl or phenyl, $R_6$ is hydrogen, $C_1$–$C_4$alkyl or phenyl, $R_7$ is hydrogen or $C_1$–$C_{10}$alkyl, $R_8$ is hydrogen, $C_1$–$C_4$alkyl or phenyl, $X_1$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or —(CH$_2$)$_r$COO—$Y_1$, $X_2$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl or $C_7$–$C_9$phenylalkyl, $X_3$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl, $C_1$–$C_{18}$alkanoyl, $C_3$–$C_{18}$alkenoyl, $C_3$–$C_{18}$alkanoyl which is interrupted by oxygen or >N—$Y_2$, $C_6$–$C_9$cycloalkylcarbonyl, benzoyl, $C_1$–$C_4$alkyl-substituted benzoyl, thenoyl or furoyl, $Y_1$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl or $C_7$–$C_9$phenylalkyl, $Y_2$ is hydrogen or $C_1$–$C_8$alkyl, p is 0, 1 or 2, q is an integer from 0 to 8, r is 1 or 2, n is an integer from 1 to 4, and, when n is 1, A is a group —O—$Z_1$, —N($Z_2$)($Z_3$), —NH(O$Z_4$), —O—N=C($Z_5$)($Z_6$), —S(O)$_m Z_7$, —NH—$Z_8$ or —S—$Z_8$, or A is also an unsubstituted or $C_1$–$C_4$alkyl-substituted heterocyclic radical which has the free valence at a nitrogen atom, $Z_1$ is hydrogen, $C_1$–$C_{18}$alkyl, $C_3$–$C_{18}$alkyl which is interrupted by oxygen or >N—$Y_2$, $C_3$–$C_{18}$alkenyl, $C_5$–$C_{18}$cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, $C_7$–$C_9$phenylalkyl, $C_7$–$C_9$phenylalkyl which is substituted at the phenyl ring by $C_1$–$C_4$alkyl; tetrahydrofurfuryl, tetrahydroabietyl, $C_1$–$C_{18}$alkanoyl, $C_3$–$C_{18}$alkenoyl, $C_3$–$C_{18}$alkanoyl which is interrupted by oxygen or >N—$Y_2$, $C_6$–$C_9$-cycloalkylcarbonyl, benzoyl, $C_1$–$C_4$alkyl-substituted benzoyl, thenoyl, furoyl or a group of formula IIa or IIb, $Z_2$ is hydrogen, $C_1$–$C_{18}$alkyl, OH-substituted $C_2$–$C_{18}$alkyl, $C_3$–$C_{18}$alkenyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl, $C_1$–$C_{18}$alkanoyl, $C_3$–$C_{18}$alkenoyl, $C_3$–$C_{18}$alkanoyl which is interrupted by oxygen or >N—$Y_2$, $C_6$–$C_9$cycloalkylcarbonyl, benzoyl, $C_1$–$C_4$alkyl-substituted benzoyl, thenoyl, furoyl, —($CH_2$)$_p$COO—$X_2$ or a radical of formula IIb, $Z_3$ is hydrogen, $C_1$–$C_{18}$alkyl, OH-substituted $C_2$–$C_{18}$alkyl, $C_3$–$C_{18}$alkenyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or a group of formula IIb, or $Z_2$ and $Z_3$, taken together, are $C_3$–$C_6$alkylene, $C_3$–$C_6$oxoalkylene or $C_3$–$C_6$alkylene which is interrupted by oxygen or >N—$T_6$, $Z_4$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted penyl or $C_7$–$C_9$phenylalkyl, $Z_5$ and $Z_6$ are each independently of the other hydrogen, $C_1$–$C_{18}$alkyl, $C_2$–$C_{18}$alkenyl, $C_5$–$C_8$cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl or $C_7$–$C_9$phenylalkyl, or $Z_5$ and $Z_6$, together with the linking carbon atom, form an unsubstituted or $C_1$–$C_4$alkyl-substituted $C_5$–$C_8$cycloalkylidene ring, $Z_7$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or —($CH_2$)$_r$COO—$Y_1$, $Z_8$ is unsubstituted or $C_1$–$C_4$alkyl-substituted 2-benzoxazolyl or unsubstituted or $C_1$–$C_4$alkyl-substituted 2-benzothiazolyl, $T_1$ and $T_2$ are each independently of the other hydrogen, $C_1$–$C_{18}$alkyl, $C_2$–$C_{18}$alkenyl, $C_5$–$C_8$cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl, $C_7$–$C_9$phenylalkyl or —$CH_2$—S—$X_1$, $T_3$ is hydrogen or $C_1$–$C_4$alkyl, $T_4$ is hydrogen, $C_1$–$C_{18}$alkyl, $C_2$–$C_{18}$alkenyl, $C_5$–$C_8$cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl, $C_7$–$C_9$phenylalkyl, —$CH_2$—S—$X_1$, —($CH_2$)$_p$COO—$X_2$ or —($CH_2$)$_q$O—$X_3$, $T_5$ is hydrogen, $C_1$–$C_4$alkyl, —OH, $C_6$–$C_{12}$alkoxy, $C_5$–$C_8$cycloalkoxy, allyl, benzyl or acetyl, $T_6$ is $C_1$–$C_{12}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl or $C_7$–$C_9$phenylalkyl, m is 1 or 2, w is 0 or 1, when n is 2, A is a group of formula IIIa, IIIb, IIIc, IIId, IIIe or IIIf, $G_1$ and $G_3$ are each independently of the other hydrogen, $C_1$–$C_{18}$alkyl, $C_3$–$C_{18}$alkenyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl, —($CH_2$)$_p$COO—$X_2$ or a radical of formula IIb, $G_2$ is $C_2$–$C_{12}$alkylene, $C_4$–$C_{12}$alkylene which is interrupted by oxygen or >N—$Y_2$, $C_4$–$C_{12}$alkenylene, $C_4$–$C_{12}$alkynylene, ($C_1$–$C_4$alkylene)phenylene-($C_1$–$C_4$alkylene), a monocyclic saturated hydrocarbon radical having two free valences and containing 5 to 12 carbon atoms, phenylene, $C_1$–$C_4$alkyl-substituted phenylene or naphthylene, $C_2$–$C_{18}$alkanedioyl, $C_4$–$C_{18}$alkenedioyl or carboxybenzoyl, $G_4$ and $G_6$ are each independently of the other hydrogen, $C_1$–$C_{18}$alkyl, $C_3$–$C_{18}$alkenyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or a group of formula IIb, $G_5$ $C_2$–$C_{12}$alkylene, $C_4$–$C_{12}$alkylene which is interrupted by oxygen or >N—$Y_2$, $C_4$–$C_{12}$alkenylene, $C_4$–$C_{12}$alkynylene, ($C_1$–$C_4$alkylene)phenylene-($C_1$–$C_4$alkylene), a monocyclic saturated hydrocarbon radical having two free valences and containing 5 to 12 carbon atoms, phenylene, $C_1$–$C_4$alkyl-substituted phenylene or naphthylene, $G_7$ is $C_2$–$C_{12}$alkylene, $C_4$–$C_{12}$alkylene which is interrupted by oxygen or >N—$Y_2$, $C_4$–$C_{12}$alkenylene, $C_4$–$C_{12}$alkynylene, ($C_1$–$C_4$alkylene)phenylene-($C_1$–$C_4$alkylene), a monocyclic saturated hydrocarbon radical having two free valences and containing 5 to 12 carbon atoms, phenylene, $C_1$–$C_4$alkyl-substituted phenylene or naphthylene, $C_2$–$C_{18}$alkanedioyl, $C_4$–$C_{18}$alkenedioyl or carboxybenzoyl $G_8$ and $G_{10}$ are each independently of the other hydrogen, $C_1$–$C_{18}$alkyl, $C_3$–$C_{18}$alkenyl, $C_5$–$C_8$-cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or a group of formula IIb, $G_9$ and $G_{11}$ are $C_2$–$C_{12}$alkylene, $C_4$–$C_{12}$alkylene which is interrupted by oxygen or >N—$Y_2$, $C_4$–$C_{12}$alkenylene, $C_4$-$C_{12}$alkynylene, ($C_1$-$C_4$alkylene)phenylene-($C_1$-$C_4$alkylene), a monocyclic saturated hydrocarbon radical having two free valences and containing 5 to 12 carbon atoms, phenylene, $C_1$-$C_4$alkyl-substituted phenylene or naphthylene, $G_{12}$ is hydrogen, $C_1$-$C_{18}$alkyl, $C_3$-$C_{18}$alkenyl, $C_5$-$C_8$-cycloalkyl, $C_1$-$C_4$alkyl-substituted $C_5$-$C_8$cycloalkyl, phenyl, $C_1$-$C_4$alkyl-substituted phenyl, $C_7$-$C_9$phenylalkyl or a group of formula IIb, and t is 1 or 2.

Likewise preferred are compounds of formula I, wherein the substituents $R_1$ are each independently of one another $C_1$-$C_{10}$alkyl, $C_2$-$C_{18}$alkenyl, $C_5$-$C_8$-cycloalkyl, $C_5$-$C_8$-cycloalkenyl, phenyl, $C_7$-$C_9$phenylalkyl or —$CH_2$—S—$X_1$, the substituents $R_2$ are each independently of one another hydrogen, $C_1$-$C_{10}$alkyl, $C_2$-$C_{18}$alkenyl, $C_5$-$C_8$cycloalkyl, $C_5$-$C_8$cycloalkenyl, phenyl, $C_7$-$C_9$phenylalkyl, —$CH_2$—S—$X_1$, —$(CH_2)_p$COO—$X_2$ or —$(CH_2)_q$O—$X_3$, the substituents $R_3$ are hydrogen, $R_4$ is hydrogen or $C_1$-$C_4$alkyl, $R_5$ is hydrogen, $C_1$-$C_4$alkyl or phenyl, $R_6$ is hydrogen, $C_1$-$C_4$alkyl or phenyl, $R_7$ is hydrogen or $C_1$-$C_4$alkyl, $R_8$ is hydrogen, $C_1$-$C_4$alkyl or phenyl, $X_1$ is $C_1$-$C_{10}$alkyl, $C_5$-$C_8$cycloalkyl, phenyl, $C_7$-$C_9$phenylalkyl or —$(CH_2)_r$COO—$Y_1$, $X_2$ is $C_1$-$C_{10}$alkyl, $C_5$-$C_8$cycloalkyl, phenyl or $C_7$-$C_9$phenylalkyl, $X_3$ is $C_1$-$C_{10}$alkyl, $C_5$-$C_8$cycloalkyl, phenyl, $C_7$-$C_9$phenylalkyl, $C_1$-$C_{10}$alkanoyl, $C_3$-$C_{18}$alkenoyl, $C_3$-$C_{18}$alkanoyl which is interrupted by oxygen; or benzoyl, $Y_1$ is $C_1$-$C_{10}$alkyl, $C_5$-$C_8$cycloalkyl, phenyl or $C_7$-$C_9$phenylalkyl, p is 0, 1 or 2, q is an integer from 0 to 8, r is 1 or 2, n is an integer from 1 to 4, and, when n is 1, A is a group —O—$Z_1$, —N($Z_2$)($Z_3$), —NH(O$Z_4$), —O—N=C($Z_5$)($Z_6$), —S(O)$_m$$Z_7$, —NH—$Z_8$ or —S—$Z_8$, or A is also an unsubstituted or $C_1$-$C_4$alkyl-substituted heterocyclic radical which has the free valence at a nitrogen atom, $Z_1$ is hydrogen, $C_1$-$C_{18}$alkyl, $C_3$-$C_{18}$alkyl which is interrupted by oxygen; $C_3$-$C_{18}$alkenyl, $C_5$-$C_8$cycloalkyl, $C_5$-$C_8$cycloalkenyl, $C_7$-$C_9$phenylalkyl, tetrahydrofurfuryl, $C_1$-$C_{10}$alkanoyl, $C_3$-$C_{18}$alkenoyl, $C_3$-$C_{18}$alkanoyl which is interrupted by oxygen; benzoyl or a group of formula IIa or IIb, $Z_2$ is hydrogen, $C_1$-$C_{18}$alkyl, OH-substituted $C_2$-$C_{10}$alkyl, $C_3$-$C_{18}$alkenyl, $C_5$-$C_8$cycloalkyl, phenyl, $C_7$-$C_9$phenylalkyl, $C_1$-$C_{10}$alkanoyl, $C_3$-$C_{18}$alkenoyl, $C_3$-$C_{18}$alkanoyl which is interrupted by oxygen; benzoyl, —$(CH_2)_p$COO—$X_2$ or a group of formula IIb, $Z_3$ is hydrogen, $C_1$-$C_{18}$alkyl, OH-substituted $C_2$-$C_{10}$alkyl, $C_3$-$C_{18}$alkenyl, $C_5$-$C_8$-cycloalkyl, phenyl, $C_7$-$C_9$phenylalkyl or a group of formula IIb, or $Z_2$ and $Z_3$, taken together, are $C_3$-$C_6$alkylene, $C_3$-$C_6$oxoalkylene or $C_3$-$C_6$alkylene which is interrupted by oxygen, $Z_4$ is $C_1$-$C_{10}$alkyl, $C_5$-$C_8$-cycloalkyl, phenyl or $C_7$-$C_9$phenylalkyl, $Z_5$ and $Z_6$ are each independently of the other hydrogen, $C_1$-$C_{10}$alkyl, $C_2$-$C_{18}$alkenyl, $C_5$-$C_8$cycloalkyl, $C_5$-$C_8$cycloalkenyl, phenyl or $C_7$-$C_9$phenylalkyl, or $Z_5$ and $Z_6$, together with the linking carbon atom, form a $C_5$-$C_8$cycloalkylidene ring, $Z_7$ is $C_1$-$C_{10}$alkyl, $C_5$-$C_8$cycloalkyl, phenyl, $C_7$-$C_9$phenylalkyl or —$(CH_2)_r$COO—$Y_1$, $Z_8$ is unsubstituted or $C_1$-$C_4$alkyl-substituted 2-benzoxazolyl or unsubstituted or $C_1$-$C_4$alkyl-substituted 2-benzothiazolyl, $T_1$ and $T_2$ are each independently of the other hydrogen, $C_1$-$C_{10}$alkyl, $C_2$-$C_{18}$alkenyl, $C_5$-$C_8$-cycloalkyl, $C_5$-$C_8$cycloalkenyl, phenyl, $C_7$-$C_9$phenylalkyl or —$CH_2$—S—$X_1$, $T_3$ is hydrogen or $C_1$-$C_4$alkyl, $T_4$ is hydrogen, $C_1$-$C_{10}$alkyl, $C_2$-$C_{18}$alkenyl, $C_5$-$C_8$cycloalkyl, $C_5$-$C_8$-cycloalkenyl, phenyl, $C_7$-$C_9$phenylalkyl, —$CH_2$—S—$X_1$, —$(CH_2)_p$COO—$X_2$ or —$(CH_2)_q$O—$X_3$, $T_5$ is $C_1$-$C_4$alkyl, —OH, $C_6$-$C_{12}$alkoxy, $C_5$-$C_8$cycloalkoxy, allyl, benzyl or acetyl, m is 1 or 2, w is 0 or 1, when n is 2, A is a group of formula IIIa, IIIb, IIIc, IIId, IIIe or IIIf, $G_1$ and $G_3$ are each independently of the other hydrogen, $C_1$-$C_{10}$alkyl, $C_3$-$C_{18}$alkenyl, $C_5$-$C_8$cycloalkyl, phenyl, $C_7$-$C_9$phenylalkyl, —$(CH_2)_p$COO—$X_2$ or a radical of formula IIb, $G_2$ is $C_2$-$C_{10}$alkylene, $C_4$-$C_{12}$alkylene which is interrupted by oxygen; $C_4$-$C_{10}$alkenylene, $C_4$-$C_{10}$alkynylene, ($C_1$-$C_4$alkylene)phenylene-($C_1$-$C_4$alkylene), a monocyclic saturated hydrocarbon radical having two free valences and containing 5 to 10 carbon atoms, phenylene, $C_2$-$C_{10}$alkanedioyl, $C_4$-$C_{10}$alkenedioyl or carboxybenzoyl, $G_4$ and $G_6$ are each independently of the other hydrogen, $C_1$-$C_{10}$alkyl, $C_3$-$C_{18}$alkenyl, $C_5$-$C_8$cycloalkyl, phenyl, $C_7$-$C_9$phenylalkyl or a group of formula IIb, $G_5$ is $C_2$-$C_{10}$alkylene, $C_4$-$C_{12}$alkylene which is interrupted by oxygen; $C_4$-$C_{10}$alkenylene, $C_4$-$C_{10}$alkynylene, ($C_1$-$C_4$alkylene)phenylene-($C_1$-$C_4$alkylene), a monocyclic saturated hydrocarbon radical having two free valences and containing 5 to 10 carbon atoms or phenylene, $G_7$ is $C_2$-$C_{10}$alkylene, $C_4$-$C_{12}$alkylene which is interrupted by oxygen; $C_4$-$C_{10}$alkenylene, $C_4$-$C_{10}$alkynylene, ($C_1$-$C_4$alkylene)phenylene-($C_1$-$C_4$alkylene), a monocyclic saturated hydrocarbon radical having two free valences and containing 5 to 10 carbon atoms, phenylene, $C_2$-$C_{10}$alkanedioyl, $C_4$-$C_{10}$alkenedioyl or carboxybenzoyl, $G_8$ and $G_{10}$ are each independently of the other hydrogen, $C_1$-$C_{10}$alkyl, $C_3$-$C_{18}$alkenyl, $C_5$-$C_8$cycloalkyl, phenyl, $C_7$-$C_9$phenylalkyl or a group of formula IIb, $G_9$ and $G_{11}$ are $C_2$-$C_{10}$alkylene, $C_4$-$C_{12}$alkylene which is interrupted by oxygen; $C_4$-$C_{10}$alkenylene, $C_4$-$C_{10}$alkynylene, ($C_1$-$C_4$alkylene)phenylene-($C_1$-$C_4$alkylene), a monocyclic saturated hydrocarbon radical having two free valences and containing 5 to 10 carbon atoms or phenylene, $G_{12}$ is hydrogen, $C_1$-$C_{10}$alkyl, $C_3$-$C_{18}$alkenyl, $C_5$-$C_8$cycloalkyl, phenyl, $C_7$-$C_9$phenylalkyl or a group of formula IIb, and t is 1 or 2.

Compounds of formula I are also preferred, wherein
n is 1,
A is a group of formula —N($Z_2$)($Z_3$),
$Z_2$ is hydrogen, and
$Z_3$ is hydrogen, $C_1$–$C_{25}$alkyl, OH-substituted $C_2$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or a group of formula IIb.

Other preferred compounds of formula I are those wherein
n is 1,
A is a group of formula —O—$Z_1$, and
$Z_1$ is $C_1$–$C_{25}$alkyl which is interrupted by oxygen; or a group of formula IIa, and
w is 1.

A further preferred embodiment of the invention comprises compounds of formula I, wherein the substituents $R_1$ are identical and are $C_1$–$C_5$alkyl or $C_5$–$C_8$cycloalkyl,
the substituents $R_2$ are identical and are $C_1$–$C_5$alkyl,
the substituents $R_3$ are hydrogen, and
$R_4$ is hydrogen or $C_1$–$C_4$alkyl.

Particularly preferred compounds of formula I are those, wherein the substituents $R_1$ are identical and are $C_1$–$C_5$alkyl or $C_5$–$C_8$cycloalkyl,
the substituents $R_2$ are identical and are $C_1$–$C_5$alkyl,
the substituents $R_3$ are hydrogen,
$R_4$ is hydrogen or $C_1$–$C_4$alkyl,
$R_5$, $R_6$, $R_7$ and $R_8$ are hydrogen,
n is 1 or 2, and,
when n is 1, A is a group —O—$Z_1$, —N($Z_2$)($Z_3$), —NH(O$Z_4$), —O—N=C($Z_5$)($Z_6$), —S(O)$_m$$Z_7$, —NH—$Z_8$ or —S—$Z_8$, or A is also an unsubstituted or $C_1$–$C_4$alkyl-substituted heterocyclic radical which has the free valence at a nitrogen atom,
$Z_1$ is $C_1$–$C_{18}$alkyl, $C_3$–$C_{10}$alkyl which is interrupted by oxygen; $C_5$–$C_8$cycloalkyl, tetrahydrofurfuryl or a group of formula IIa or IIb,
$Z_2$ is $C_1$–$C_{18}$alkyl, —OH-substituted $C_2$–$C_4$alkyl, $C_7$–$C_9$phenylalkyl, —(CH$_2$)$_p$COO—$X_2$ or a radical of formula IIb,
$Z_3$ is hydrogen, $C_1$–$C_{18}$alkyl, —OH-substituted $C_2$–$C_4$alkyl, $C_7$–$C_9$phenylalkyl or a radical of formula IIb, or
$Z_2$ and $Z_3$, taken together, are $C_3$–$C_6$oxoalkylene or $C_3$–$C_6$alkylene which is interrupted by oxygen,
$Z_4$ is $C_7$–$C_9$phenylalkyl,
$Z_5$ and $Z_6$, together with the linking carbon atom, form a $C_5$–$C_8$cycloalkylidene ring,
$Z_7$ is $C_1$–$C_{10}$alkyl,
$Z_8$ is unsubstituted or $C_1$–$C_4$alkyl-substituted 2-benzoxazolyl or unsubstituted or $C_1$–$C_4$alkyl-substituted 2-benzothiazolyl,
$T_1$, $T_2$, $T_3$ and $T_4$ are each independently of the other hydrogen or $C_1$–$C_4$alkyl,
$T_5$ is hydrogen or $C_1$–$C_4$alkyl,
$X_2$ is $C_1$–$C_{10}$alkyl,
m is 1 or 2,
p is 1,
w is 0 or 1, and
when n is 2, A is a group of formula IIIa, IIIc or IIIf,
$G_1$ and $G_3$ are each independently of the other hydrogen, $C_7$–$C_9$phenylalkyl or a radical of formula IIb,
$G_2$ is $C_2$–$C_8$alkylene or a monocyclic saturated hydrocarbon radical with two free valences and containing 10 carbon atoms,
$G_7$ is $C_2$–$C_8$alkylene or $C_4$–$C_{12}$alkylene which is interrupted by oxygen, and
$G_{12}$ is $C_7$–$C_9$phenylalkyl or a group of formula IIb.

The compounds of formula I may be prepared by the following per se known processes:

Process A:
Reaction of a compound of formula a

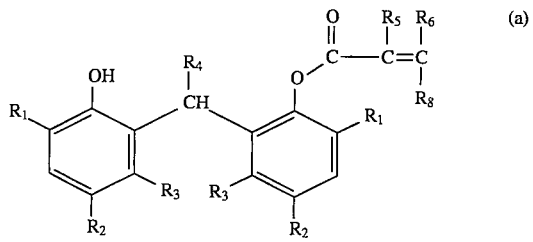

with a suitable compound of formula b (Michael addition),

in which formulae above $R_1$ to $R_8$ and A as well as the index n are as defined for formula I.

The reaction can be carried out by mixing the two reactants, with or without a solvent. Suitable solvents are customary hydrocarbons (e.g. toluene, hexane and cyclohexane), halogenated hydrocarbons (e.g. dichloromethane, dichloroethane and chlorobenzene), ethers (e.g. diethyl ether, dibutyl ether, tetrahydrofuran find dimethoxyethane), alcohols e.g. methanol and ethanol) and also acetonitrile, butyl acetate and dimethyl formamide.

The reaction is preferably carried out in the temperature range from 5° C. to the boiling point of the reaction mixture.

When adding an alcohol (or a mercaptan) to the compound of formula a it is preferred to add catalytic amounts of a base (0.5–30 mol %) to the reaction mixture. Suitable bases typically include alkali metal hydroxides, $C_1$–$C_5$alkali metal alkoxides, amines (e.g. triethylamine, N,N-dimethylaniline, N-methylaniline and pyridine), tetraalkylammonium hydroxides or benzyltrimethylammonium hydroxide or also organometallic compounds (e.g. BuLi).

Compounds of formula I, wherein A is a group —S(O)$_m$$Z_7$, may be obtained by reacting a bisphenol monoacrylate of formula a with a mercaptan of formula b (A=S$Z_7$) and subsequently oxidising the resultant thioether by standard methods (q.v. inter alia Comprehensive Organic Chemistry, Vol 3, p. 124–126, 174, Ed. D. Neville Jones, Pergamon Press, 1979).

Process B:
Esterification or transesterification of organic carboxylic acid derivatives of formula c

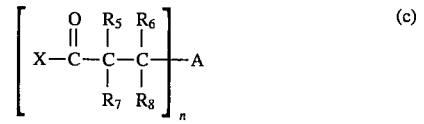

with bisphenols of formula d,

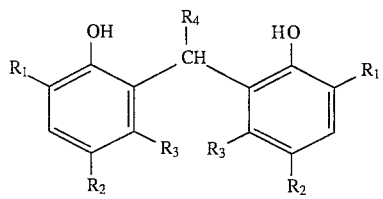
(d)

in which formulae above $R_1$ to $R_8$ and A as well as the index n are as defined for formula I

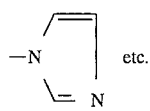 etc.

The reaction can be carried out in per se known manner, conveniently by adding one of the two educts to the second educt and thoroughly mixing both reactants, preferably excluding oxygen. The reaction can be carried out with or without a solvent (e.g. toluene). The temperature may be in the range from the melting point to the boiling point of the reaction mixture, suitably in the range from −50° to 150° C., preferably from 0° to 150° C. The purification of the resultant product can likewise be effected by known methods, typically by washing with water/HCl, extraction with an organic solvent, crystallisation and/or chromatography. Preferred solvents for the extraction and for the chromatographic purification step are hexane, ethyl acetate or mixtures thereof.

If an acid chloride (X=Cl) is used in the reaction as derivative of the carboxylic acid of formula c, then an acid acceptor can also be added to the reaction mixture. Suitable acid acceptors are typically amines such as pyridine or triethylamine. The amount of acid acceptor is preferably at least equivalent to the amount of acid chloride and is typically 1 to 2 equivalents, preferably 1.2 to 1.7 equivalents, based on the acid chloride.

The acid chloride can also be prepared "in situ", in which case the carboxylic acid of formula c (X=OH), the bisphenol of formula d and an acid acceptor (e.g. triethylamine) are charged to the reactor and then the phosphoroxy chloride is added in analogy to the process described in U.S. Pat. No. 5,128,398.

If the carboxylic acid of formula c and the bisphenol of formula d are used direct as educts, then the reaction is conveniently carried out using a reagent that absorbs water of reaction, typically dicyclohexylcarbodiimide.

Process C:

Reaction of a chloride of formula e

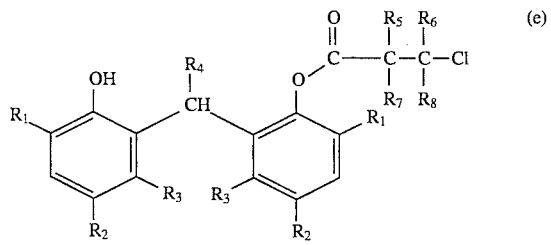
(e)

with a compound of formula b, preferably in the presence of a base as acid acceptor. Suitable acid acceptors are amines (such as triethylamine and pyridine), hydrides (such as lithium, sodium and potassium hydride), alcoholates (such as sodium methanolate and potassium tert-butylate) and organometallic bases (such as BuLi).

If the base is a hydride, an alkali metal, alkali metal hydroxide, alkali metal alcoholate or alkyl lithium compound, then the corresponding anion of the compound of formula b can be formed first.

Illustrative examples of compounds of formula I are listed in the following Table 1.

TABLE 1

| Compound | Structure | Elemental analysis Mass spectrum Melting point | | | |
|---|---|---|---|---|---|
| 101 | (structure with HN—CH₂—C₅H₆ ester group, phenol with (H₃C)₃C, C(CH₃)₃, CH₃ substituents) | Elemental analysis calcd: found: Melting point 124–126° C. | C % 79.00 79.03 | H % 8.64 8.61 | N % 2.79 2.74 |
| 102 | (structure with N(CH₂—C₅H₆)₂ ester group, phenol with (H₃C)₃C, C(CH₃)₃, CH₃ substituents) | Elemental analysis: calcd: found: Mass spectrum: (CI): 592(MH⁺) | C % 81.18 80.34 | H % 8.35 8.59 | N % 2.37 2.85 |
| 103 | (structure with N-methyl tetramethylpiperidine, C₄H₉-n, ester linked to phenol with C(CH₃)₃, CH₃ substituents) | Mass spectrum (DEI): 620(M⁺) Melting point 38–43° C. | | | |
| 104 | (structure with N-methyl tetramethylpiperidine, C₄H₉-n, ester linked to phenol with t-C₅H₁₁ substituents) | Elemental analysis calcd: found: | C % 79.01 78.57 | H % 11.18 11.36 | N % 3.61 3.37 |

TABLE 1-continued

| Compound | Structure | Elemental analysis Mass spectrum Melting point | | |
|---|---|---|---|---|
| 105 | [structure with N—CH₂—C₅H₆ group]₂ | Elemental analysis calcd: found: Melting point 70–76° C. | C % 79.07 78.70 | H % 8.66 8.75 | N % 1.56 1.35 |
| 106 | [structure with 2,2,6,6-tetramethylpiperidine N—CH₃]₂ | Elemental analysis calcd: found: Melting point 89–94° C. | C % 77.62 77.09 | H % 9.46 9.45 | N % 2.92 2.76 |
| 107 | [structure with tetramethylpiperidinyl N—(CH₂)₃ group]₂ | Elemental analysis calcd: found: Melting point 83–86° C. | C % 77.11 76.52 | H % 10.05 9.99 | N % 4.73 4.47 |

TABLE 1-continued

| Compound | Structure | Elemental analysis<br>Mass spectrum<br>Melting point |
|---|---|---|
| 108 | (structure: bis-compound with 2,2,6,6-tetramethylpiperidin-4-yl-N-(CH₂)₃- group linked via ester to phenol bearing CH₃, C₅H₁₁-t substituents, methylene-bridged to another phenol with OH, t-C₅H₁₁ groups; bracketed ×2) | Elemental analysis<br>calcd:   C% 78.87   H% 10.94   N% 3.75<br>found:   78.82   10.88   3.66<br>Melting point<br>66–67° C. |
| 109 | (structure: ester of phenol bearing CH₃, C(CH₃)₃ and -N(C₄H₉-n)₂-terminated propanoate, methylene-bridged to phenol with OH, C(CH₃)₃, (H₃C)₃C) | Elemental analysis<br>calcd:   C% 79.17   H% 10.86   N% 2.25<br>found:   78.96   10.96   2.19<br>Melting point<br>89–90° C. |
| 110 | (structure: ester of phenol bearing CH₃, C(CH₃)₃ and -N(CH₂CH₂OH)₂-terminated propanoate, methylene-bridged to phenol with OH, C(CH₃)₃, (H₃C)₃C) | Elemental analysis<br>calcd:   C% 74.33   H% 9.95   N% 2.34<br>found:   74.50   10.11   2.24<br>Melting point<br>136–138° C. |

TABLE 1-continued

| Compound | Structure | Elemental analysis<br>Mass spectrum<br>Melting point |
|---|---|---|
| 111 | [structure with bis-phenol, CH₂–C₅H₆, N–CH₂, t-C₅H₁₁, C₅H₁₁-t groups, dimer] | Elemental analysis<br>calcd: C% 80.91, H% 9.81, N% 2.10<br>found: C% 80.72, H% 9.92, N% 2.04<br>Melting point 129–134° C. |
| 112 | [structure with morpholine-N-propyl ester of bis-phenol with C(CH₃)₃ groups] | Elemental analysis<br>calcd: C% 76.64, H% 9.91, N% 2.42<br>found: C% 76.65, H% 9.91, N% 2.37<br>Melting point 150–152° C. |
| 113 | [structure with HN–C₈H₁₇-n substituent on bis-phenol with C(CH₃)₃ groups] | Elemental analysis<br>calcd: C% 79.17, H% 10.86, N% 2.25<br>found: C% 79.02, H% 10.74, N% 2.12<br>Melting point 102–104° C. |
| 114 | [structure with HN–C₁₂H₂₅-n substituent on bis-phenol with C(CH₃)₃ groups] | Elemental analysis<br>calcd: C% 79.71, H% 11.15, N% 2.07<br>found: C% 79.45, H% 10.96, N% 1.92<br>Melting point 85–86° C. |

TABLE 1-continued

| Compound | Structure | Elemental analysis<br>Mass spectrum<br>Melting point |
|---|---|---|
| 115 | (structure with HN—C₁₆H₃₃-n chain) | Elemental analysis<br>calcd: C% 80.16, H% 11.40, N% 1.91<br>found: C% 80.10, H% 11.39, N% 1.70<br>Melting point 62–64° C. |
| 116 | (structure with HN—C₁₈H₃₇-n chain) | Elemental analysis<br>calcd: C% 80.36, H% 11.50, N% 1.84<br>found: C% 80.37, H% 11.55, N% 1.79<br>Melting point 64–69° C. |
| 117 | (structure with NH—COOC₂H₅ chain) | Elemental analysis<br>calcd: C% 74.58, H% 9.64, N% 2.35<br>found: C% 74.61, H% 9.90, N% 2.37<br>Melting point 121–122° C. |
| 118 | (bis structure with HN—(CH₂)₃— bridge, subscript 2) | Elemental analysis<br>calcd: C% 78.50, H% 10.25, N% 2.54<br>found: C% 78.43, H% 10.20, N% 2.58<br>Melting point 148° C. |

TABLE 1-continued

| Compound | Structure | Elemental analysis<br>Mass spectrum<br>Melting point |
|---|---|---|
| 119 | [structure: bis(3,5-di-tert-butyl-2-(1-(3,5-di-tert-butyl-2-hydroxyphenyl)ethyl)phenyl propanoate) linked via HN—(CH$_2$)$_4$—NH] | Elemental analysis<br>calcd: C% 79.12, H% 10.13, N% 2.43<br>found: C% 78.58, H% 10.52, N% 2.40<br>Melting point<br>72–75° C. (amorph) |
| 120 | [structure: bis-ester linked via 1,4-cyclohexyl bis(C(CH$_3$)$_2$NH—)] | Elemental analysis<br>calcd: C% 78.98, H% 10.29, N% 2.42<br>found: C% 78.26, H% 10.43, N% 2.42<br>Melting point<br>102–108° C. (amorph) |
| 121 | [structure: 3,5-di-tert-butyl-2-(1-(3,5-di-tert-butyl-2-hydroxyphenyl)ethyl)phenyl 3-(2-oxopiperidin-1-yl)propanoate] | MS (DCI): MH$^+$ 592<br>IR (KBr):<br>1740.7 cm$^{-1}$ (—O—C(=O)—)<br>1629.4 cm$^{-1}$ (—N—C(=O)—)<br>Melting point 217–223° C. |
| 122 | [structure: ester with HN—O—CH$_2$—C$_5$H$_6$ substituent] | Elemental analysis<br>calcd: C% 78.01, H% 9.33, N% 2.27<br>found: C% 77.74, H% 9.33, N% 2.27<br>Melting point<br>123° C. |

TABLE 1-continued

| Compound | Structure | Elemental analysis<br>Mass spectrum<br>Melting point |
|---|---|---|
| 201 | (structure with 2,2,6,6-tetramethyl-N-methylpiperidin-4-yloxy group, propanoate ester of 2-[1-(2-hydroxy-3-tert-butyl-5-tert-butylphenyl)ethyl]-4-tert-butyl-6-tert-butylphenol) | Elemental analysis<br>calcd:  C % 76.42  H % 9.80  N % 2.48<br>found:  76.06  9.72  2.40<br>Melting point<br>104–105° C. |
| 202 | (similar structure with tert-amyl (C₅H₁₁-t) groups instead of tert-butyl) | Elemental analysis<br>calcd:  C % 78.02  H % 10.96  N % 1.98<br>found:  78.00  10.71  1.88<br>Melting point<br>46–47° C. |
| 203 | (structure with cyclohexyloxy group and tert-amyl substituents) | Elemental analysis<br>calcd:  C % 79.83  H % 10.56<br>found:  79.58  10.53<br>Melting point<br>101–105° C. |
| 204 | (structure with O—C₈H₁₇-n group and tert-butyl substituents) | Elemental analysis<br>calcd:  C % 79.05  H % 10.68<br>found:  79.04  11.08<br>Melting point<br>114–115° C. |

TABLE 1-continued

| Compound | Structure | Elemental analysis<br>Mass spectrum<br>Melting point | | |
|---|---|---|---|---|
| 205 | ![structure with O—C₄H₉-n] | Elemental analysis<br>calcd:<br>found: | C %<br>78.40<br>78.45 | H %<br>10.31<br>10.32 |
| | | Melting point<br>85–87° C. | | |
| 206 | ![structure with O—C₁₀H₂₁-n] | Elemental analysis<br>calcd:<br>found: | C %<br>79.33<br>79.34 | H %<br>10.84<br>10.98 |
| | | Melting point<br>69–71° C. | | |
| 207 | ![structure with O—C₁₂H₂₅-n] | Elemental analysis<br>calcd:<br>found: | C %<br>79.59<br>79.30 | H %<br>10.98<br>11.26 |
| | | Melting point<br>71–73° C. | | |
| 208 | ![structure with O-cyclohexyl] | Elemental analysis<br>calcd:<br>found: | C %<br>79.01<br>78.54 | H %<br>10.20<br>10.27 |
| | | Melting point<br>87–91° C. | | |

TABLE 1-continued

| Compound | Structure | Elemental analysis Mass spectrum Melting point | | |
|---|---|---|---|---|
| 209 | (structure with CH₃, C₆H₁₃, C(CH₃)₃ groups) | Elemental analysis calcd: found: Melting point 64–74° C. | C % 79.05 79.10 | H % 10.68 10.69 |
| 210 | (structure with O—C₁₈H₃₇-n, C(CH₃)₃ groups) | Elemental analysis calcd: found: Melting point 65–67° C. | C % 80.26 80.29 | H % 11.36 11.33 |
| 211 | (structure with O—(CH₂CH₂O)₂—C₂H₅, C(CH₃)₃ groups) | Elemental analysis calcd: found: Melting point 74–78° C. (amorph) | C % 74.72 74.53 | H % 9.97 10.02 |
| 212 | (structure with O—(CH₂—CH₂—O)₂—C₄H₉-n, C(CH₃)₃ groups) | Elemental analysis calcd: found: | C % 75.19 75.12 | H % 10.16 10.19 |

TABLE 1-continued

| Compound | Structure | Elemental analysis<br>Mass spectrum<br>Melting point |
|---|---|---|
| 213 | [structure] | Elemental analysis<br>calcd: C% 74.08 H% 9.91<br>found: 74.10 9.91<br>Melting point 65–66° C. |
| 214 | [structure] | Elemental analysis<br>calcd: C% 79.12 H% 9.79<br>found: 79.27 9.99 |
| 214 bis | [structure] | Elemental analysis<br>calcd: C% 78.05 H% 9.27<br>found: 77.96 9.25<br>Melting point 103–105° C. |
| 215 | [structure] | Elemental analysis<br>calcd: C% 76.68 H% 10.23<br>found: 76.56 10.56<br>Melting point 88–91° C. |

TABLE 1-continued

| Compound | Structure | Elemental analysis / Mass spectrum / Melting point |
|---|---|---|
| 216 | [structure: bis-ester with central CH₂-O-CH₂CH₂- linker connecting two 3-(3-methyl-5-tert-butyl... wait; phenolic propanoate units with ortho-CH(CH₃)- bridge to 3-methyl-5-tert-butyl-2-hydroxyphenyl] | Elemental analysis<br>calcd: C% 78.07, H% 9.88<br>found: C% 78.04, H% 9.84<br>Melting point 94° C. |
| 217 | [analogous bis-ester with –O–CH₂–C(CH₃)₂–CH₂–O– type central linker]₂ | Elemental analysis<br>calcd: C% 77.02, H% 9.79<br>found: C% 76.92, H% 9.67<br>Melting point 72–73° C. |
| 218 | [bis-ester with –(O–CH₂CH₂CH₂CH₂)₃–O– linker]₂ | Elemental analysis<br>calcd: C% 76.80, H% 10.08<br>found: C% 75.54, H% 10.29<br>Melting point 51–53° C. |
| 219 | [ester of 2,4-di-tert-butylphenoxy-propanoate with 3-methyl-5-tert-butyl-2-hydroxyphenyl-CH(CH₃)- bridge] | Elemental analysis<br>calcd: C% 80.75, H% 10.09<br>found: C% 80.62, H% 10.12<br>Melting point 185° C. |

TABLE 1-continued

| Compound | Structure | Elemental analysis Mass spectrum Melting point |
|---|---|---|
| 220 | (structure with phenoxy group) | Elemental analysis<br>calcd: C % 79.82, H % 9.28<br>found: C % 79.70, H % 9.33<br>Melting point 113–116° C. |
| 221 | (structure with cyclohexylideneaminooxy group) | Elemental analysis<br>calcd: C % 77.31, H % 9.82, N % 2.31<br>found: C % 77.07, H % 9.57, N % 2.22<br>Melting point 118–121° C. |
| 222 | (structure with isopropoxyethoxy group) | Elemental analysis<br>calcd: C % 76.47, H % 10.13<br>found: C % 76.37, H % 10.39<br>Melting point 98° C. |
| 223 | (structure with tetrahydrofurfuryloxy group) | Elemental analysis<br>calcd: C % 76.72, H % 9.83<br>found: C % 75.99, H % 9.68<br>Melting point 91–93° C. |

TABLE 1-continued

| Compound | Structure | Elemental analysis Mass spectrum Melting point |
|---|---|---|
| 224 | [structure with OC₂H₅, C(CH₃)₃ groups and phenolic ring] | Elemental analysis<br>calcd: C % 76.47  H % 10.13<br>found: C % 76.35  H % 10.25<br>Melting point<br>83–85° C. |
| 225 | [structure with isopropoxy group, C(CH₃)₃ groups] | Elemental analysis<br>calcd: C % 76.68  H % 10.23<br>found: C % 76.45  H % 10.33<br>Melting point<br>117–120° C. |
| 301 | [structure with S(=O)–C₈H₁₇ sulfoxide group] | Elemental analysis<br>calcd: C % 73.34  H % 9.41  S % 5.76<br>found: C % 72.83  H % 9.41  S % 5.30<br>Melting point |
| 302 | [structure with S(=O)₂–C₈H₁₇ sulfone group] | Elemental analysis<br>calcd: C % 71.29  H % 9.15  N % 5.60<br>found: C % 71.36  H % 9.23  N % 5.65<br>Melting point<br>108–113° C. |

TABLE 1-continued

| Compound | Structure | Elemental analysis<br>Mass spectrum<br>Melting point |
|---|---|---|
| 401 | [structure: bis-phenol methane with propanoate ester linked to imidazole, with C(CH₃)₃ and CH₃ substituents] | Elemental analysis<br>calcd: C% 74.83, H% 9.15, N% 7.48<br>found: C% 74.77, H% 9.22, N% 7.03<br>Melting point 160–162° C. |
| 402 | [structure: bis-phenol methane with propanoate ester linked to imidazole, with C(CH₃)₃ substituents] | Elemental analysis<br>calcd: C% 77.10, H% 9.35, N% 5.00<br>found: C% 76.94, H% 9.40, N% 4.91<br>Melting point 88–92° C. |
| 403 | [structure: bis-phenol methane with propanoate ester linked to benzotriazole, with C(CH₃)₃ substituents] | Elemental analysis<br>calcd: C% 76.56, H% 8.73, N% 6.87<br>found: C% 76.30, H% 8.70, N% 6.87<br>Melting point 174–178° C. |
| 404 | [structure: bis-phenol methane with propanoate ester linked to tolyltriazole (CH₃-substituted benzotriazole), with C(CH₃)₃ substituents] | Elemental analysis<br>calcd: C% 76.76, H% 8.86, N% 6.71<br>found: C% 76.22, H% 9.20, N% 6.57<br>Melting point 81–84° C. |

TABLE 1-continued
| Compound | Structure | Elemental analysis<br>Mass spectrum<br>Melting point | | | |
|---|---|---|---|---|---|
| 405 | 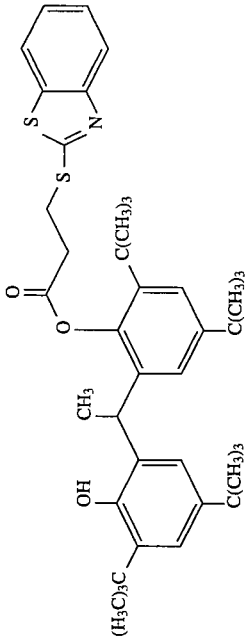 | Elemental analysis<br>calcd:<br>found:<br><br>Melting point<br>123–128° C. | C %<br>72.80<br>72.58 | H %<br>8.09<br>8.08 | N %<br>2.12<br>2.16 | S %<br>9.72<br>9.79 |
Compounds 113, 116, 117, 215 and 222 are particularly preferred embodiments of the invention.

The compounds of formula I are suitable for stabilising organic materials against thermal, oxidative or light-induced degradation. Illustrative examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (uncrosslinked or crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with diglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyether imides, polyester imides, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention thus also relates to a composition comprising an organic material stabilised against oxidative, thermal or light-induced degradation and at least one compound of formula I.

The organic material is preferably a synthetic polymer, more particularly one selected from the aforementioned groups. Polyolefins and a solution-polymerised polybutadiene rubber are particularly preferred. A further particularly preferred organic material is a solution-polymerised styrene-butadiene copolymer or styrene-butadiene block copolymer in which the ratio of styrene to conjugated butadiene is conveniently 5:95 to 95:5. The polybutadiene component in these copolymers is c. 5 to 30%. A preferred organic material is also acrylonitrile-butadiene-styrene.

The compounds of formula I are usually incorporated in the material to be stabilised in amounts of 0.01 to 10%, preferably 0.01 to 5%, most preferably 0.05 to 0.5%, based on the total weight of the material to be stabilised.

The novel compounds are incorporated in the organic material by known methods, conveniently before or during shaping to moulded articles or alternatively by coating the organic material with a solution or dispersion of the compounds and subsequently removing any solvent used by evaporation. The novel compounds can be incorporated in the material to be stabilised as powder, granulate or also in the form of a masterbatch which contains these compounds in a concentration of 2.5 to 25% by weight.

The compounds of formula I can also be incorporated in the organic material before or during polymerisation or before crosslinking.

The stabilised materials may be in any form of presentation, typically sheets, filaments, ribbons, mouldings, profiles or binders for coating compositions, adhesives or putties.

Further different customary additives may also be incorporated in the stabilised organic materials, typically including:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-ten-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris( 5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxy phenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.7 O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetale.

1.8. Hydroxybenzylated malonates, for example dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl-2,2-bis-(3,5-di-tert-butyl-4-hydroxybenzyl)malonate, bis[4(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanutrate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxy ethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxy phenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.21]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.21]octane.

1.17. Amides of β-(3,5-di-tert-butyl-4-hydroxy phenyl)propionic acid, e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenyleneaIiamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octylphenothiazines, N-allylphenothiazine, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)-carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—$COO(CH_2)_3$]$_2$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines., for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis( 1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, the condensate of N,N'-bis(2,2,6,6-tetra-methyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-bis(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy and 4-stearyloxy-2,2,6,6-tetramethylpiperidine, a condensation product of N,N'-bis-(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6- pentamethyl-4-piperidyl)-n-dodecylsuccinimide, 2-undecyl-7,7,9,9-tetramethyl-1-oxa- 3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and the mixture thereof with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8.2-(2-Hyrdoroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis-(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyldibenzo[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-hepta-decyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, e.g. calcium stearate, zinc stearate, magnesium behenate, magnesium stearate, sodium ricinoleate and potassium palmitate, antimony pyrocatecholate or tin pyrocatecholate.

11. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass beads, asbestos, talc, kaolin, mica, barium sulfate, metal oxides and hydroxides, carbon black, graphite, sawdust or fibers of other natural products, synthetic fibers.

13. Other additives, for example, plasticisers, lubricants, emulsifiers, pigments, rheology additives, catalysts, flow-control agents, fluorescent whitening agents, flame-proofing agents, antistatic agents and blowing agents.

14. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one.

The weight ratio of the novel stabiliser to the customary additive may be 1:0.5 to 1:5.

A further object of the invention is the use of the novel stabilisers for stabilising organic material against oxidative, thermal or light-induced degradation.

The invention is illustrated in more detail by the following Examples in which percentages are by weight, unless otherwise indicated.

EXAMPLE 1

Preparation of compound 101 (Process A)

7.2 g (18 mmol) of 2,2'-methylenebis[6-tert-butyl-4-methylphenol] monoacrylate are dissolved in 70 ml of dichloromethane. Then 2.17 ml (20 mmol) of benzylamine are slowly added dropwise at room temperature (RT) to this solution. Afterwards the mixture is further stirred for 3 hours at RT. The solvent is stripped off and the residue is chromatographed over silica gel (eluant: hexane), affording 6.63 g (66%) of compound 101 as a white powder. The melting point is 124°–126° C.

Compounds 102–104 are prepared in accordance with the method described in this Example.

EXAMPLE 2

Preparation of compound 105 (process A).

16.57 g (42 mmol) of 2,2'-methylenebis[6-tert-butyl-4-methylphenol] monoacrylate and 2.17 ml (20 mmol) of benzylamine in 150 ml dichloroethane are charged, under argon, to a round-bottomed flask fitted with magnetic stirrer and condenser. The reaction mixture is refluxed overnight and subsequently concentrated on a vacuum rotary evaporator. Chromatography of the residue over silica gel (eluant: hexane→Hex/EA 80:1; Hex=hexane, EA=ethyl acetate) yields 12.44 g (69%) of compound 105 as a white powder. The melting point is 70°–76° C.

Compounds 106–110 are prepared in accordance with the method described in this Example.

EXAMPLE 3

Preparation of compound 111 (process A).

A mixture of 4.6 g (8.3 mmol) 2,2'-ethylidenebis[4,6-di-tert-amylphenol] monoacrylate and 1 g (4.16 mmol) of N,N'-dibenzylethylenediamine is stirred for 4 hours at 140° C. The reaction mixture is cooled to RT and the crude product is chromatographed over silica gel (eluant: hexane), affording 5.15 g (93%) of compound 111 as an amorphous powder. The melting point is 129°–134° C.

EXAMPLE 4

Preparation of compound 112 (process C).

a) Preparation of 2,4-di-tert-butyl-6-[1-(3,5-di-tert-butyl-2-hydroxyphenyl)ethyl]phenyl 3-chloropropionate

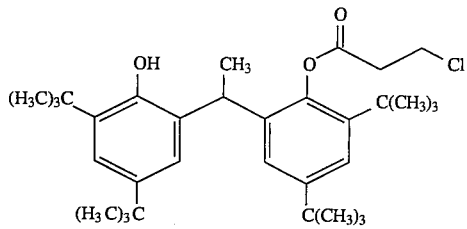

112a 21.9 g (50 mmol) of 2,2'-ethylidenebis[4,6-di-tert-butylphenol] and 48 ml (500 mmol) of 3-chloropropionyl chloride in 100 ml xylene are charged to a 250 ml round bottomed flask fitted with magnetic stirrer, condenser and bubble counter. The mixture is refluxed for 15 hours (evolution of HCl). Excess acid chloride and the toluene are removed by distillation. Crystallisation of the residue in acetonitrile yields 15.8 g (60%) of the desired monoester 112 a as a beige powder. The melting point is 118°–121° C.

| | Elemental analysis: | | |
|---|---|---|---|
| | C % | H % | Cl % |
| calcd: | 74.90 | 9.33 | 6.70 |
| found: | 75.10 | 9.29 | 6.13 | b) 1.63 g (18.7 mmol) of morpholine are added dropwise at RT and under nitrogen to a stirred solution of 4.5 g (8.5 mmol) of compound 112a (Example 4a) in 30 ml of toluene. The reaction mixture is stirred for 1 hour at 70° C., cooled to RT, filtered over Hyflo and concentrated by evaporation.

Crystallisation of the residue in hexane gives 3.9 g (80%) of compound 112 as a white powder. The melting point is 150°–152° C.

EXAMPLE 5

Preparation of compound 113 (process A).

A mixture of 19.7 g (0.04 mol) of 2,2'-ethylidenebis[4,6-di-tert-butylphenol] monoacrylate (preparation as described in EP-A-500 323) and 6.72 g (0.052 mol) of octylamine is heated to 115° C. The colourless solution so obtained is stirred for 30 minutes at this temperature. Then 50 ml of ethanol are added. The batch is cooled to RT, whereupon the product crystallises out. The crystalline product is isolated by filtration and dried under vacuum, affording 21.9 g (88%) of compound 113 as a white powder.

The melting point is 102–104° C.

Compounds 114, 115 and 116 are prepared in general accordance with the procedure of this Example.

EXAMPLE 6

Preparation of compound 117 (process A).

6.41 g (13 mmol) of 2,2'-ethylidenebis[4,6-di-tert-butylphenol]monoacrylate, 2 g (14.3 mmol) of glycine ethyl ester hydrochloride and 50 ml of ethylene chloride are charged, under nitrogen, to a 200 ml sulfonation flask fitted with thermometer, stirrer, reflux condenser and dropping funnel. Then 2 ml (1.45 g, 14.3 mmol) of triethylamine are added dropwise. When this addition is complete, the mixture is heated to 50° C. and stirred for 5 hours at this temperature. The resultant suspension is diluted with 25 ml of hexane and the salts are removed by filtration. The solvent is stripped off on a vacuum rotary evaporator and the crude product is crystallised from hexane, affording 3.7 g (48%) of compound 117 as a white powder. The melting point is 121°–122° C.

EXAMPLE 7

Preparation of compound 118 (process A).

A mixture of 6.92 g (14 mmol) of 2,2'-ethylidenebis[4,6-di-tert-butylphenol]monoacrylate, and 0.89 g (7.7 mmol) of 1,6-diaminohexane in 40 ml of ethyl acetate is refluxed for 30 minutes. The solvent is then removed by evaporation. Crystallisation of the residue from acetonitrile yields 5 g (65%) of compound 118 as a white powder. The melting point is 148° C.

EXAMPLE 8

Preparation of compound 121 (process B).

A mixture of 2.05 g (12 mmol) of 3-[2-oxo-piperidino] propionic acid (q.v. Dado, G. P; Gellman, S.H.; J. Am. Chem. Soc., 116(3), 1054–62, 1994), 4.4 g (10 mmol) of 2,2'-ethylidenebis[4,6-di-tert-butylphenol], 2.06 g (10 mmol) of dicyclohexylcarbodiimide and 50 mg of dimethylaminopyridine in 60 ml of dichloroethane is refluxed for 15 hours. The precipitated urea is removed by filtration and the solvent is stripped off. Crystallisation of the residue from a 1:1 mixture of hexane/ethyl acetate, yields 2.6 g (44%) of compound 121 as a white powder. The melting point is 217°–223° C.

EXAMPLE 9

Preparation of compound 122 (process A).

A mixture of 6.6 g (13 mmol) of 2,2'-ethylidenebis[4,6-di-tert-butylphenol]monoacrylate, 4 g (23.5 mmol) of O-benzyl-hydroxylamine hydrochloride and 38 ml (27 mmol) of triethylamine in 70 ml of dichloroethane is refluxed for 8 hours at 65° C. The reaction mixture is diluted with c. 10 ml of hexane, the salts are removed by filtration, and solvent is distilled off on a vacuum rotary evaporator. Crystallisation of the residue from methanol yields 4.6 g (55%) of compoudg 122 as a white powder. The melting point is 123° C.

EXAMPLE 10

Preparation of compound 201 (process A).

5.65 g (33 mmol) of 4-hydroxy-1,2,2,6,6-pentamethylpiperidine in 85 ml of tetrahydrofuran are charged to a 250 ml round bottomed flask which is blanketed with nitrogen. The solution is cooled to 0° C. and 5.6 ml (9 mmol) of a 1.6N solution of butyllithium in hexane are slowly added dropwise. The resultant white suspension is stirred for 30 minutes, and then a solution of 11.84 g (30 mmol) of 2,2'-ethylidenebis[4,6-di-tert-butylphenol]monoacrylate in 85 ml of tetrahydrofuran is slowly added dropwise. The yellow solution is stirred for 3 hours at RT. The reaction mixture is then concentrated by evaporation and the residue is poured into an aqueous saturated solution of ammonium chloride. After repeated extraction with ethyl acetate the organic phases are combined, dried over potassium carbonate and concentrated on a vacuum rotary evaporator. Chromatography of the residue ($SiO_2$:Hex/EA9:1→1:1) yields 11.06 g (65%) of compound 201 as a white powder. The melting point is 104°–105° C.

Compounds 202 and 203 are prepared in general accordance with the procedure described in Example 4.

EXAMPLE 11

Preparation of compound 204 (process B).

a) Preparation of 3-octyloxypropionic acid 21.7 ml (0.33 mol) of acrylonitrile are added dropwise at RT over 25 minutes and under $N_2$ to a colourless solution of 39.1 g (0.3 mol) of octanol and 1.2 ml (2.9 tool) of benzyltrimethylammonium hydroxide (40% solution in water)(exothermic reaction: Ti 40° C.). When this addition is complete, the reaction mixture is stirred for a further 25 minutes at RT. Excess acrylonitrile is removed by destillation (vacuum rotatary evaporator). The resultant crude 3-octyloxypropionitrile (pale yellow liquid; 97% GC) is dissolved in 150 ml of conc. hydrochloric acid and 150 ml of acetic acid and the solution is heated for 3 hours to 85° C. The mixture is cooled and poured into 100 ml of water. After extraction with ethyl acetate, the organic phase is separated, washed with an aqueous saturated solution of NaCl, dried over $Na_2SO_4$, and concentrated on a vacuum rotary evaporator, affording 60 g of 3-octyloxypropionic acid as a colourless liquid (85% GC→85% yield).

| Elemental analysis: | | |
|---|---|---|
| | C % | H % |
| calcd: | 65.31 | 10.96 |
| found: | 64.94 | 11.09 | b) 7.08 g (35 mmol) of 3-octyloxypropionic acid (q.v. Example 11 a) in 50 ml of toluene are charged, under argon, to a 100 ml round bottomed flask fitted with magnetic stirrer and condenser. To this solution are added 7.6 ml (18.5 g, 105 mmol) of thionyl chloride. The mixture is slowly heated to 90° C. (evolution of HCl and $SO_2$) and stirred for 2 hours at this temperature. Stirring is then continued for a further 30 minutes while introducing a stream of argon. Under reduced pressure (20 mbar) excess thionyl chloride and the toluene are removed by distillation. The residue (7 g of 3-octyloxypropionyl chloride) is dissolved in 50 ml of toluene and 10.97 g (25 mmol) of 2,2'-ethylidenebis[4,6-di-tert-butylphenol] are added. Then 4.9 ml (35 mmol) of triethylamine are added dropwise to this solution at 10° C. After c. 10 minutes the mixture is warmed to RT and stirred for 1 hour for 30 minutes at RT. The reaction mixture is filtered over Celite and the filtrate is concentrated on a vacuum rotary evaporator. The residue is taken up in c. 30 ml of acetonitrile, whereupon compound 204 crystallises. The product is collected by suction filtration and dried, affording 14.05 g (90%) of compound 204 as a white powder. The melting point is 114° C.

The preparation of compounds 205 to 214 is carried out in general accordance with the procedure of this Example.

EXAMPLE 12

Preparation of compound 204 (Process B).

6.6 g (15 mmol) of 2,2'-ethylidenebis[4,6-di-tert-butylphenol], 3.8 g (15 mmol) of 3-octyloxypropionic acid and 6 ml of heptane are charged, under $N_2$ to a 100 ml sulfonation flask fitted with thermometer, stirrer, reflux condenser and dropping funnel. Then 4.4 ml (31.5 mmol) triethylamine are added dropwise to this suspension (the suspension goes into solution), followed by the dropwise addition of 0.96 ml (10.5 mmol) of phosphoroxy chloride (exothermic reaction: Ti 60° C.). The suspension so obtained is heated for 1 hour to 80° C. After cooling to RT, 10 ml of water are added (the salts dissolve). The organic phase is separated, washed with water, dried over $Na_2SO_4$ and concentrated on a vacuum rotary evaporator. Crystallisation of the residue (c. 10 g) in 20 ml of acetonitrile yields 6.8 g (73%) of compound 204 as a white powder. The melting point is 114°–115° C.

EXAMPLE 13

Preparation of compound 204 (process B).

12.18 g (0.05 mol) of 3-octyloxypropionic acid (83% GC), 4.7 ml (0.065 mol) of thionyl chloride and 0.11 g (0.5 mmol) of benzyltriethylammonium chloride are charged to a 50 ml round bottomed flask fitted with magnetic stirrer and condenser. The colourless solution is stirred for 10 minutes at RT (evolution of HCl+$SO_2$; endothermic reaction: Ti 12° C.). The reaction mixture is then heated to 65° C. under a weak stream of $N_2$ and further stirred for 45 minutes at this temperature. Excess thionyl chloride is removed by distillation (70°–80° C./40 mbar; 30 minutes). To the resultant colourless liquid (crude acid chloride) are added 18 g (0.041 mol) of 2,2'-ethylenebis[4,6-di-tert-butylphenol]. The mixture is heated to 140° C. (evolution of HCl) and stirred for 30 minutes at this temperature. Stirring is then continued under a weak stream of $N_2$ for 1 hour. The resultant brown liquid is cooled to c. 100° C. and 70 ml of ethanol are added. The batch is cooled in an ice bath, whereupon the product crystallises out. The crystalline product is isolated by filtration and dried under a high vacuum, affording 20 g (78%) of compound 204 as a white powder. The melting point is 115° C.

EXAMPLE 14

Preparation of compound 215 (process B).

a) Preparation of 3-(2-butoxyethoxy)propionic acid 2 ml (3.2 mmol, 10 mol %) of a 1.6N solution of butyllithium in hexane are added dropwise, under $N_2$, at 10° C. to a solution of 3.8 g (32 mmol) of 2-butoxyethanol in 2 ml of tetrahydrofuran. The solution is stirred for 5 minutes at 10° C. Then 2.5 ml (38 mmol) of acrylonitrile are added. The reaction mixture is heated to 55° C. and stirred for 2.5 hours at this temperature. Then a further 0.25 ml (3.8 mmol) of acrylonitrile is added and the mixture is stirred for another hour at 55° C. The reaction mixture is cooled to RT and afterwards poured into water. After acidification with 2N HCl (2 ml) and extraction with toluene, the organic phase is washed with an aqueous saturated solution of NaCl, dried over magnesium sulfate and concentrated on a vacuum rotary evaporator. The crude 3-(2-buthoxyethoxy)propionitrile (4.4 g) is taken up in 15 ml of concentrated hydrochloric acid and the solution is heated for 2.5 hours to 80° C. The resultant brown solution is cooled to RT, diluted with water and and extracted once more with ethyl acetate. The organic phases are combined, washed with an aqueous saturated solution of NaCl, dried over $MgSO_4$, concentrated on a vacuum rotary evaporator and dried under a high vacuum, affording 3.2 g (53%) of 3-(2-butoxyethoxy)propionic acid as a pale brown liquid.

$^1$H-NMR (300 MHz; $CDCl_3$): δ (ppm) 0.91 (t, J=7.3 Hz, 3H); 1,36 (sextet, J=7.6 Hz, 2H); 1.57 (quintet, J=7.8 Hz, 2H); 2.65 (t, J=6.3 Hz, 2H); 3.47 (t, J=6.6 Hz, 2H); 3.56–3.65 (dxm, 4H); 3.77 (t, J=6.3 Hz, 2H); 9.6 (s, wide, 1H).

b) A solution of 3.1 g (15 mmol) of dicyclohexylcarbodiimide in 10 ml of ethylene chloride is added dropwise at RT under $N_2$ to a solution of 6.6 g (15 mmol) of 2,2'-ethylidenebis[4,6-di-tert-butylphenol], 3.76 g (18 mmol) of 3-(2-butoxyethoxy)propionic acid and 0.1 g (0.8 mmol, 5 mol %) of dimethylaminopyridine in 60 ml of ethylene chloride. The reaction mixture is stirred for 15 hours at RT. The precipitated urea is removed by filtration and the solvent is removed by evaporation. Crystallisation of the residue from acetonitrile yields 5 g (54%) of compound 215 as a white powder. The melting point is 88°–91° C.

EXAMPLE 15

Preparation of compound 216 (process B).

a) 10.02 g (55 mmol) of 3-[3-(2-carboxyethoxy)propoxy]propanoic acid (q.v. R.V. Christian and R.M. Hixon J.A.C.S. 70, 1333, (1948)) in 100 ml of toluene are charged to a 250 ml round botomed flask under nitrogen. To this suspension are added 13.2 ml (180 mmol) of thionyl chloride and the mixture is slowly heated (over 40 minutes) to 90° C. (evolution of $HCl+SO_2$) and stirred for 1 hour at this temperature. Stirring is then continued for another 45 minutes at 90° C. while introducing a stream of argon. Distillation of excess thionyl chloride and toluene yields the crude bis-acid chloride, which is further used direct.

b) The bis-acid chloride described in Example 15a (55 mmol) and 43.87 g (0.1 mol) of 2,2'-ethylidenebis[4,6-di-tert-butylphenol] in 100 ml of toluene are charged to a 350 ml sulfonation flask under argon. This solution is cooled to 10° C. and 16.7 ml (120 mmol) of triethylamine are slowly added dropwise. When this addition is complete (c. 50 minutes), the mixture is heated to 70° C. and further stirred overnight at this temperature.

The precipitated triethylamine hydrochoride is removed by filtration and the filtrate is concentrated by evaporation. Chromatography of the residue over silica gel (eluant: Hex/EE 40:1 ) yields 21 g (40% ) of compound 216 as an amorphous powder. The melting point is 94° C.

Compounds 217 and 218 are prepared in general accordance with the method described in this Example.

EXAMPLE 16

Preparation of compound 219 (Process B).

a) Preparation of 3-(2,4-di-tert-butylphenoxy)propionic acid 6.2 ml (94 mmol) of acrylonitrile are added dropwise at room temperature under $N_2$ over 20 minutes to a solution of 9.7 g (47 mmol) of 2,4-di-tert-butylphenol and 0.6 ml (1.5 mmol) of benzyltrimethylammonium hydroxide (40% solution in water). When this addition is complete, the reaction mixture is heated to 65° C. and stirred for 2.5 hours at this temperature. Excess acrylonitrile is subsequently removed by distillation (vacuum rotatary evaporator). The crude 3-(2,4-di-tert-butylphenoxy)propionitrile is dissolved in 40 ml of conc. hydrochloric acid and 40 ml of acetic acid and the solution is heated for 10 hours to 100° C. The mixture is cooled, poured into 60 ml of water and extracted with a 1:1 mixture of hexane/ethyl acetate. The organic phase is separated, washed with an aqueous saturated solution of NaCl, dried over sodium sulfate and concentrated on a vacuum rotary evaporator. Distillation of the residue (60° C./0.1 mbar) yields 10 g (77%) of the desired acid as a whiteish-beige powder. The melting point is 105°–106° C.

$^1$H-NMR (300 MHz) $CDCl_3$: δ=2,89 (t, J=6.2 Hz, 20H; —$CH_2$—COOH—), 4.27 (t,J=6.2 Hz, 2H, A—O—$CH_2$—).

b) 10 g (36 mmol) of 3-(2,4-di-tert-butylphenoxy)propionic acid, 13.1 g (30 mmol) of 2,2'-ethylidenebis[4,6-di-tert-butylphenol], 0.2 g (1.6 mmol, 5 mol %) of dimethylaminopyridine and 180 ml of dichloroethane are charged to a round bottomed flask fitted with condenser and magnetic stirrer. Then a solution of 6.2 g (30 mmol) of dicyclohexylcarbodiimide in 20 ml of dichloroethane are added dropwise to this solution at RT and under $N_2$. The mixture is stirred for 15 hours at RT. The precipitated urea is removed by filtration and the solvent is stripped off. Crystallisation of the residue from hexane yields 10 g (48%) of compound 219 as a white powder. The melting point is 185° C.

Compound 220 is prepared from commercially available 3-phenoxypropionic acid and 2,2'-ethylidenebis[4,6-di-tert-butylphenol] in analogy to the process described in Example 16b.

EXAMPLE 17

Preparation of compound 221 (process B).

a) Preparation of 3-cyclohexylideneaminoxypropionic acid

A mixture of 32.8 g (0.29 mol) of cyclohexanone oxime, 26 g (0.26 mmol) of ethyl acrylate, 26 ml (0.052 mol) of a 2N solution of KOH in ethanol and 150 ml of ethanol is stirred for 96 hours at 60° C. and afterwards concentrated on a vacuum rotary evaporator. The residue (an orange oil) is dissolved in 175 g (0.31 tool) of a 10% solution of KOH in ethanol and the solution is heated for 1 hour to 60° C. The solvent is distilled off and the solid residue is taken up in water. After acidification with c. 15 ml of conc. hydrochloric acid and extraction with ethyl acetate, the organic phase is washed with water, dried over $Na_2SO_4$ and concentrated on a vacuum rotary evaporator. Distillation of the residue yields 11.8 g (25%) of the desired acid as an orange liquid. The boiling point is 135° C./0.05 mbar.

| Elemental analysis: | | |
|---|---|---|
| C % | calcd: 58.36 | found: 58.47 |
| H % | calcd: 8.16 | found: 8.30 |
| N % | calcd: 7.56 | found: 7.13 | b) Starting from 8.03 g (39 mmol) of 3-cyclohexylidene-aminooxypropionic acid and 15.34 g (35 mmol) of 2,2'-ethylidenebis[4,6-di-tert-butylphenol] and carrying out the procedure as described in Example 16b there are obtained 15.3 g (72%) of compound 221 as a white powder. The melting point is 118°–121° C. (methanol).

Compounds 222–224 are prepared in analogy to the method described in Example 13 (process B).

Compound 225 is prepared in analogy to the method described in Example 14b (process B).

EXAMPLE 18

Preparation of compound 301 (oxidation of the thioether obtained in process A)

a) Preparation of 2-tert-butyl-6-(3-tert-butyl-2-hydroxy-5-methylphenylmethyl)-4-methylphenyl 3-(octylthio)propanoate In a 200 ml sulfonation flask, 9.86 g (25 mmol) of 2,2'-methylenebis[6-tert-butyl-4-methylphenol]monoacrylate and 4.02 g (27.5 mmol) of octanethiol are dissolved in 50 ml of toluene. Then 0.75 ml (1.25 mmol) of a 1.7N solution of potassium tert-pentylate in toluene is added dropwise at RT. Afterwards the reaction mixture is heated to c. 55° C. and stirred for 1 hour at this temperature. The mixture is cooled to RT and poured into dilute hydrochloric acid (0.1N). After repeated extraction with ethyl acetate the organic phases are combined, dried over sodium sulfate and concentrated on a vacuum rotary evaporator. Unreacted bisphenol is removed (bulb tube distillation at 200° C./10 mbar), giving 11.35 g (84%) of the desired compound as a pale yellow oil.

| Elemental analysis: | | | | | |
|---|---|---|---|---|---|
| C % | calcd: 75.51 | H % | calcd: 9.69 | S % | calcd: 5.93 |
| | found: 75.31 | | found: 9.84 | | found: 6.05 | b) In a 250 ml sulfonation flask, 10.82 g (20 mmol) of the compound of Example 18a are dissolved, under nitrogen, in 130 ml of dichloromethane. Then a solution of 6.59 g (21 mmol) of m-chloroperbenzoic acid in 70 ml of dichloromethane are added dropwise to this solution at −15° C. The reaction mixture is stirred for 30 minutes at −15° C. and poured into an aqueous saturated solution of sodium hydrogencarbonate. After repeated extraction with dichloromethane, the organic phases are combined, washed with water, dried over sodium sulfate and concentrated on a vacuum rotary evaporator. The residue is dried under a high vacuum, affording 11.13 g (100%) of compound 301 as a colourless highly viscous oil.

EXAMPLE 19

Preparation of compound 302 (oxidation of the thioether obtained in process A)

In a 250 ml sulfonation flask, 10.82 g (20 mmol) of the compound of Example 18 are dissolved, under nitrogen, in 80 ml of dichloromethane.

A solution of 13.82 g (42 mmol) of m-chloroperbenzoic acid in 120 ml of dichloromethane is added dropwise to this solution at −15° C. The thick suspension is further stirred until it has warmed to RT and then poured into an aqueous saturated solution of sodium hydrogencarbonate. After repeated extraction with dichloromethane, the organic phases are combined, washed with water, dried over sodium sulfate and concentrated on a vacuum rotary evaporator. Crystallisation of the residue from isopropanol yields 8.05 g (70%) of compound 302 as a pale beige powder. The melting point is 108°–113° C.

EXAMPLE 20

Preparation of compound 401 (process A).

A mixture of 12.3 g (0.025 mol) of 2,2'-ethylidenebis[4,6-di-tert-butylphenol]monoacrylate, 2.07 g (0.03 mol) of 1,2,4-triazole and a few drops of pyridine is stirred for 3 hours at 150° C. The reaction mixture is then cooled to c. 100° C. and, after addition of c. 30 ml of isopropanol, filtered hot. Upon cooling to room temperature, compound 401 crystallises out. The crystalline product is collected by suction filtration and dried, affording 9.10 g (65%) of compound 401 as a white powder. The melting point is 160°–162° C.

Compound 402 is prepared in analogy to the method described in Example 20, except that the reaction is carried out at 170° C. instead of 150° C.

EXAMPLE 21

Preparation of compound 403 (process B).

0.68 ml (1.15 g; 7.5 mmol) of phosphoryl chloride is added dropwise at 50° C. under $N_2$ to a colourless solution of 4.39 g (10 mmol) of 2,2'-ethylidenebis[4,6-di-tert-butylphenol], 2.5 g (13 mmol) of 3-benzotriazol-1-yl-propionic acid (Wiley et al; J. A. C. S. 76, 4933 (1954)) and 2.02 g (20 mmol) of triethylamine in 40 ml of tetrahydrofuran. The resultant suspension is stirred for 5 hours under reflux. The reaction mixture is cooled to room temperature, filtered to remove the salts and concentrated on a vacuum rotary evaporator. The residue is poured into water and, after two extractions with ethyl acetate, the organic phases are combined, washed with an aqueous saturated solution of NaCl, dried over sodium sulfate and concentrated on a vacuum rotary evaporator.

Crystallisation of the residue from ethanol yields 3.9 g (80%) of compound 403 as a white powder. The melting point is 174°–178° C.

EXAMPLE 22

Preparation of compound 404 (process A).

A mixture of 14.78 g (0.03 mol) of 2,2'-ethylidenebis[4,6-di-tert-butylphenol]monoacrylate, 5.02 g (0.03 tool) of 2-mercaptobenzothiazole and a few drops of pyridine in 25 ml of dichloroethane is stirred under reflux for 15 hours. The reaction mixture is concentrated on a vacuum rotary evaporator. Purification by chromatography ($SiO_2$; hexane/ethyl acetate: 40:1) and crystallisation from acetonitrile give 7.65 g (39%) of compound 404 as a white powder. The melting point is 123°–128° C.

EXAMPLE 22a

Preparation of compound 405.

A solution of 14.78 g (0.03 mol) of 2,2'-ethylidenebis[4,6-di-tert-butylphenol]monoacrylate, 5.02 g of 2-mercaptobenzothiazole and a few drops of pyridine in 25 ml of dichloroethane is stirred under reflux at 90° C. for 15 hours. The reaction mixture is concentrated on a vacuum rotary evaporator. Purification by chromatography ($SiO_2$; hexane/ethyl acetate: 40:1) gives 7.7 g (39%) of compound 405 as an amorphous powder. The melting point is 123°–128° C. after crystallisation in acetonitrile.

EXAMPLE 23

Stabilisation of multiple-extruded polypropylene 1.3 kg of polypropylene powder (Profax 6501), which has been prestabilised with 0.025% of n-octadecyl 3-[3,5-di-tert-butyl-4-hydroxyphenyl]propionate (melt index 3.2 g/10 min, measured at 230° C./2.16 kg) are blended with 0.05% of pentaerythritol tetrakis[3-(3,5-di-tert-butyl-4-hydroxyphenyl)propionate, 0.05% of calcium stearate, 0.03% of dihydrotalcite ($[Mg_{4.5}Al_2(OH)_{13}CO_3.3,5H_2O]$) and 0.05% of a compound of Table 1. This blend is then extruded in an extruder having a cylinder diameter of 20 mm and a length of 400 mm at 100 rpm, the 3 heating zones being adjusted to the following temperatures: 260°, 270°, 280° C. The extrudate is cooled by drawing it through a water bath and is then granulated. This granulate is repeatedly extruded. After 3 extrusions, the melt index is measured (at 230° C./2.16 kg). A substantial increase in the melt index denotes pronounced chain degradation, i.e. poor stabilisation. The results are shown in Table 2.

TABLE 2

| Compound of Table 1 | Melt index after 3 extrusions |
|---|---|
| — | 20.0 |
| 101 | 7.7 |
| 106 | 8.0 |
| 107 | 7.5 |
| 108 | 7.5 |
| 109 | 6.2 |
| 110 | 6.2 |
| 301 | 7.4 |

EXAMPLE 24

Stabilisation of elastomers (Brabender test)

A styrene-butadiene-styrene elastomer (®Finaprene 902) is blended with the stabiliser indicated in Table 3 and the blend is kneaded in a Brabender plastograph at 200° C. and 60 rpm. The kneading resistance is recorded continuously as torque. After initially remaining constant, the torque increases rapidly in the course of the kneading time owing to the crosslinking of the polymer. A prolongation of the time the torque remains constant is a measure of the effectiveness of the stabilisers. The values obtained are reported in Table 3.

TABLE 3

| 0.25% of stabiliser of Table 1 | Time in minutes until increase in torque |
|---|---|
| — | 24.2 |
| 113 | 63.3 |
| 114 | 60.0 |
| 115 | 53.5 |
| 116 | 56.6 |
| 118 | 68.4 |
| 119 | 54.0 |

EXAMPLE 25

Stabilisation of styrene-butadiene block polymers.

Thermal oxidative damage of styrene-butadiene block polymers results in a crosslinking of the rubber phase. In the course of processing in an extruder or in an injection moulding machine, this crosslinking results in an increase in the melt viscosity and therefore in the extrusion pressure.

The test of the processing stability of styrene-butadiene block polymers is often carried out in a capillary rheometer. In this test, the polymer—as similarly in extrusion—is forced through a nozzle as melt.

25 g of a styrene-butadiene block polymer granulate (®K-Resin KR-01, ex ®Phillips Petroleum) containing 0.2% of n-octadecyl-3-[3',5'-di-tert-butyl-4'-hydroxyphenyl]propionate and 0.6% of tris[nonylphenyl]phosphite are dissolved in 250 ml of cyclohexane at room temperature. The amount of stabiliser shown in Table 4 is dissolved in toluene and added to the polymer solution. The cyclohexane is stripped off at 60° C./0.013 bar.

The resultant polymer is compression moulded at 180° C. to 2 mm sheets from which circular specimens 8 mm in diameter are punched out. These specimens are placed in the receiver channel of a ®Keyeness Galaxy V capillary rheometer and measured at 250° C. and at a shear rate of 14,594 $sec^{-1}$. After 6 minutes the apparent shear rate is recorded over 30 minutes as a function of the time. The slope of this curve ($\Delta\eta/\Delta t$ in [Pa sec/min]) is a measure of the degree of crosslinking of the polymer and is therefore directly linked to the action of the stabiliser. The smaller this value is, the more effective the stabiliser. The results are shown in Table 4.

TABLE 4

| 0.15% of stabiliser of Table 1 | $\frac{\Delta\eta(Pa\ sec)}{\Delta t(min)}$ |
|---|---|
| — | 23 |
| 113 | 2 |
| 114 | 8 |
| 116 | 5 |
| 117 | 5 |
| 214 bis | 6 |
| 215 | 2 |
| 216 | 6 |

What is claimed is:
1. A compound of formula I

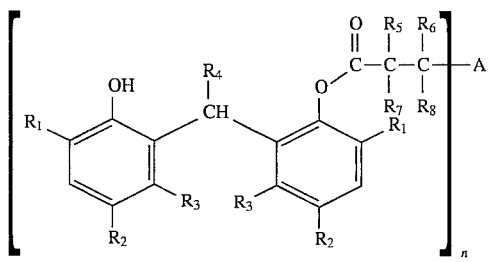

wherein
the substituents $R_1$ are each independently of one another $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl, $C_7$–$C_9$phenylalkyl or —$CH_2$—S—$X_1$, the substituents $R_2$ are each independently of one another hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl, $C_7$–$C_9$phenylalkyl, —$CH_2$—S—$X_1$, —$(CH_2)_p$COO—$X_2$ or —$(CH_2)_q$O—$X_3$, the substituents $R_3$ are each independently of one another hydrogen or $C_1$–$C_4$alkyl, $R_4$ is hydrogen or $C_1$–$C_8$alkyl, $R_5$ is hydrogen, $C_1$–$C_{10}$alkyl, phenyl, —$CH_2$—COO—$X_4$ or CN, $R_6$ is hydrogen, $C_1$–$C_4$alkyl, phenyl, —COO—$X_5$, —CN or —CON($X_6$)($X_7$), $R_7$ is hydrogen or $C_1$–$C_{10}$alkyl, $R_8$ is hydrogen, $C_1$–$C_4$alkyl or phenyl, $X_1$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or —$(CH_2)_r$COO—$Y_1$, $X_2$, $X_4$ and $X_5$ are each independently of one another $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, $X_3$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl, $C_1$–$C_{25}$alkanoyl, $C_3$–$C_{25}$alkenoyl, a $C_3$–$C_{25}$alkanoyl which is interrupted by oxygen, sulfur or >N—$Y_2$, $C_6$–$C_9$cycloalkylcarbonyl, benzoyl, $C_1$–$C_4$alkyl-substituted benzoyl, thenoyl or furoyl, $X_6$ and $X_7$ are each independently of the other hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl or $C_7$–$C_9$phenylalkyl, $Y_1$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, $Y_2$ is hydrogen or $C_1$–$C_8$alkyl, p is 0, 1 or 2, q is an integer from 0 to 8, r is 1 or 2, n is an integer from 1 to 4, and, when n is 1, A is a group —O—$Z_1$, —N($Z_2$)($Z_3$), —NH(O$Z_4$), —O—N=C($Z_5$)($Z_6$), —S(O)$_m$$Z_7$, —NH—$Z_8$ or —S—$Z_8$, or A is also an unsubstituted or $C_1$–$C_4$alkyl-substituted heterocyclic radical which has the free valence at a nitrogen atom, $Z_1$ is hydrogen, $C_1$–$C_{25}$alkyl, $C_3$–$C_{25}$alkyl which is interrupted by oxygen, sulfur or >N—$Y_2$, $C_3$–$C_{24}$alkenyl, a monocyclic saturated hydrocarbon radical containing 5 to 20 carbon atoms, a bicyclic saturated hydrocarbon radical containing 7 to 20 carbon atoms, a tricyclic saturated hydrocarbon radical containing 10 to 20 carbon atoms, $C_5$–$C_{12}$cycloalkenyl, $C_1$–$C_4$alkyl-substituted $C_5$$C_{12}$cycloalkenyl, $C_7$–$C_9$phenylalkyl, $C_7$–$C_9$phenylalkyl which is substituted at the phenyl ring by $C_1C_4$alkyl; tetrahydrofurfuryl, tetrahydroabietyl, $C_1$–$C_{25}$alkanoyl, $C_3$–$C_{25}$alkenoyl, $C_3$–$C_{25}$alkanoyl which is interrupted by oxygen, sulfur or >N—$Y_2$, $C_6$–$C_9$cycloalkylcarbonyl, benzoyl, $C_1$–$C_4$alkyl-substituted benzoyl, thenoyl, furoyl or a group of formula IIa or IIb,

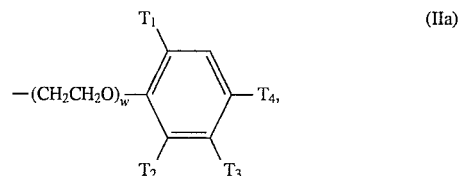

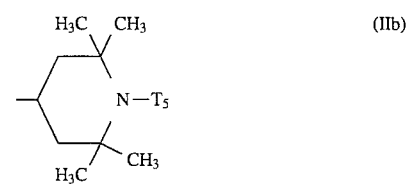

$Z_2$ is hydrogen, $C_1$–$C_{25}$alkyl, OH-substituted $C_2$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl, $C_1$–$C_{25}$alkanoyl, $C_3$–$C_{25}$alkenoyl, $C_3$–$C_{25}$alkanoyl which is interrupted by oxygen, sulfur or >N—$Y_2$, $C_6$–$C_9$cycloalkylcarbonyl, benzoyl, $C_1$–$C_4$alkyl-substituted benzoyl, thenoyl, furoyl, —$(CH_2)_p$COO—$X_2$ or a radical of formula IIb, $Z_3$ is hydrogen, $C_1$–$C_{25}$alkyl, OH-substituted $C_2$–$C_{25}$alkyl, $C_3$–$C_{24}$alkenyl, $C_5$–$C_{12}$cycloalkyl, $C_1$–$C_4$alkyl-substituted $C_5$ –$C_{12}$cycloalkyl, phenyl, $C_1$–$C_4$alkyl-substituted phenyl, $C_7$–$C_9$phenylalkyl or a group of formula IIb, or $Z_2$ and $Z_3$, taken together, are $C_3$–$C_6$alkylene, $C_3$–$C_6$oxoalkylene or $C_3$–$C_6$alkylene which is interrupted by oxygen, sulfur or >N—$T_6$, $Z_4$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, $Z_5$ and $Z_6$ are each independently of the other hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl or $C_7$–$C_9$phenylalkyl, or $Z_5$ and $Z_6$, together with the linking carbon atom, form an unsubstituted or a $C_1$–$C_4$alkyl-substituted $C_5$–$C_{12}$cycloalkylidene ring, $Z_7$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or —$(CH_2)_r$COO—$Y_1$, $Z_8$ is unsubstituted or $C_1$–$C_4$alkyl-substituted 2-benzoxazolyl or unsubstituted or $C_1$–$C_4$alkyl-substituted 2-benzothiazolyl, $T_1$ and $T_2$ are each independently of the other hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl, $C_7$–$C_9$phenylalkyl or —$CH_2$—S—$X_1$, $T_3$ is hydrogen or $C_1$–$C_4$alkyl, $T_4$ is hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl, $C_7$–$C_9$phenylalkyl, —$CH_2$—S—$X_1$, —$(CH_2)_p$COO—$X_2$ or —$(CH_2)_q$O—$X_3$, $T_5$ is hydrogen, $C_1$–$C_8$alkyl, —OH-substituted $C_2$–$C_4$alkyl, O, —OH, —NO, —$CH_2$CN, $C_1$–$C_{18}$alkoxy, $C_5$–$C_{12}$cycloalkoxy, $C_3$–$C_6$alkenyl, $C_7$–$C_9$phenylalkyl, $C_7$–$C_9$phenylalkyl which is substituted at the phenyl ring by $C_1$–$C_4$alkyl; $C_1$–$C_8$alkanoyl, $C_3$–$C_8$alkenoyl or benzoyl, $T_6$ is $C_1$–$C_{12}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, m is 1 or 2, w is 0 or 1, when n is 2, A is a group of formula IIIa, IIIb, IIIc, IIId, IIIe or IIIf,

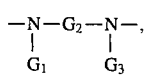 (IIIa)

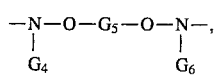 (IIIb)

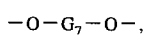 (IIIc)

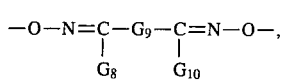 (IIId)

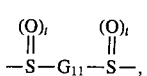 (IIIe)

 (IIIf)

$G_1$ and $G_3$ are each independently of the other hydrogen, $C_1$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl, —$(CH_2)_p$COO—$X_2$ or a radical of formula IIb, $G_2$ is $C_2$–$C_{12}$alkylene, $C_4$–$C_{20}$alkylene which is interrupted by oxygen, sulfur or >N—$Y_2$, $C_4$–$C_{20}$alkenylene, $C_4$–$C_{20}$alkynylene, ($C_1$–$C_4$alkylene)-phenylene-($C_1$–$C_4$alkylene), a monocyclic saturated hydrocarbon radical with two free valences and containing 5 to 12 carbon atoms, a bicyclic saturated hydrocarbon radical with two free valences and containing 7 to 30 carbon atoms, phenylene, $C_1$–$C_4$alkyl-substituted phenylene, naphthylene, $C_2$–$C_{20}$alkanedioyl, $C_4$–$C_{20}$alkenedioyl or carboxybenzoyl, $G_4$ and $G_6$ are each independently of the other hydrogen, $C_1$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or a group of formula IIb, $G_5$ is $C_2$–$C_{12}$alkylene, $C_4$–$C_{20}$alkylene which is interrupted by oxygen, sulfur or >N—$Y_2$, $C_4$–$C_{20}$alkenylene, $C_4$–$C_{20}$alkynylene, ($C_1$–$C_4$alkylene)-phenylene-($C_1$–$C_4$alkylene), a monocyclic saturated hydrocarbon radical with two free valences and containing 5 to 12 carbon atoms, a bicyclic saturated hydrocarbon radical with two free valences and containing 7 to 30 carbon atoms, phenylene, $C_1$–$C_4$alkyl-substituted phenylene or naphthylene, $G_7$ is $C_2$–$C_{20}$alkylene, $C_4$–$C_{20}$alkylene which is interrupted by oxygen, sulfur or >N—$Y_2$, $C_4$–$C_{20}$alkenylene, $C_4$–$C_{20}$alkynylene, ($C_1$–$C_4$alkylene)-phenylene-($C_1$–$C_4$alkylene), a monocyclic saturated hydrocarbon radical with two free valences and containing 5 to 12 carbon atoms, a bicyclic saturated hydrocarbon radical with two free valences and containing 7 to 30 carbon atoms, phenylene, $C_1$–$C_4$alkyl-substituted phenylene or naphthylene, $C_2$–$C_{20}$alkanedioyl, $C_4$–$C_{20}$alkenedioyl, carboxybenzoyl or a group of formula IVa, IVb or IVc

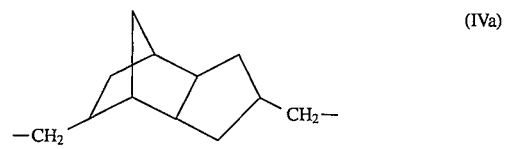 (IVa)

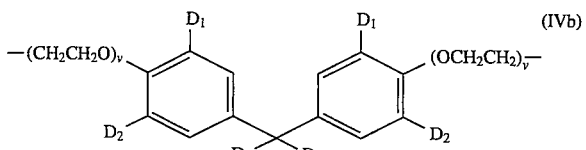 (IVb)

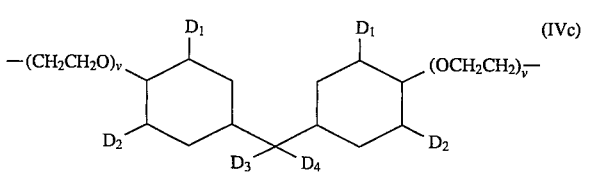 (IVc)

$G_8$ and $G_{10}$ are each independently of the other hydrogen, $C_1$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or a group of formula IIb, $G_9$ and $G_{11}$ are $C_2$–$C_{12}$alkylene, $C_4$–$C_{20}$alkylene which is interrupted by oxygen, sulfur or >N—$Y_2$, $C_4$–$C_{20}$alkenylene, $C_4$–$C_{20}$alkynylene, ($C_1$–$C_4$alkylene)-phenylene-($C_1$–$C_4$alkylene), a monocyclic saturated hydrocarbon radical with two free valences and containing 5 to 12 carbon atoms, a bicyclic saturated hydrocarbon radical with two free valences and containing 7 to 30 carbon atoms, phenylene, $C_1$–$C_4$alkyl-substituted phenylene or naphthylene, $G_{12}$ is hydrogen, $C_1$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or a group of formula IIb, the substituents $D_1$ are each independently of the other hydrogen, $C_1$–$C_8$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, the substituents $D_2$ are each independently of the other hydrogen, $C_1$–$C_8$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl, $D_3$ and $D_4$ are each independently of the other hydrogen, $CF_3$, $C_1$–$C_{12}$alkyl or phenyl, or $D_3$ and $D_4$, together with the linking carbon atom, form an unsubstituted or $C_1$–$C_4$alkyl-substituted $C_5$–$C_{12}$cycloalkylidene ring, t is 1 or 2, v is 0 or 1, when n is 3, A is a group of formula Va, Vb or Vc,

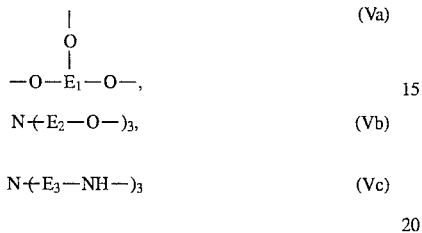

$E_1$ is $C_3$–$C_7$alkanetriyl, $E_2$ and $E_3$ are $C_2$–$C_8$alkylene, when n is 4, A is a group of formula VI

and $E_4$ is $C_4$–$C_{10}$alkanetetrayl or $C_4$–$C_{10}$alkanetetrayl which is interrupted by oxygen.

2. A compound according to claim 1, wherein the substituents $R_1$ are each independently of one another $C_1$–$C_{18}$alkyl, $C_2$–$C_{18}$alkenyl, $C_5$–$C_8$-cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl, $C_7$–$C_9$phenylalkyl or —$CH_2$—S—$X_1$, the substituents $R_2$ are each independently of one another hydrogen, $C_1$–$C_{18}$alkyl, $C_2$–$C_{18}$alkenyl, $C_5$–$C_8$-cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl, $C_7$–$C_9$phenylalkyl, —$CH_2$—S—$X_1$, —$(CH_2)_p$COO—$X_2$ or —$(CH_2)_q$O—$X_3$, the substituents $R_3$ are each independently of one another hydrogen or $C_1$–$C_4$alkyl, $R_4$ is hydrogen or $C_1$–$C_8$alkyl, $R_5$ is hydrogen, $C_1$–$C_{10}$alkyl or phenyl, $R_6$ is hydrogen, $C_1$–$C_4$alkyl or phenyl, $R_7$ is hydrogen or $C_1$–$C_{10}$alkyl, $R_8$ is hydrogen, $C_1$–$C_4$alkyl or phenyl, $X_1$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or —$(CH_2)_r$COO—$Y_1$, $X_2$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl or $C_7$–$C_9$phenylalkyl, $X_3$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl, $C_1$–$C_{18}$alkanoyl, $C_3$–$C_{18}$alkenoyl, $C_3$–$C_{18}$alkanoyl which is interrupted by oxygen or >N—$Y_2$, $C_6$–$C_9$cycloalkylcarbonyl, benzoyl, $C_1$–$C_4$alkyl-substituted benzoyl, thenoyl or furoyl, $Y_1$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl or $C_7$–$C_9$phenylalkyl, $Y_2$ is hydrogen or $C_1$–$C_8$alkyl, p is 0, 1 or 2, q is an integer from 0 to 8, r is 1 or 2, n is an integer from 1 to 4, and, when n is 1, A is a group —O—$Z_1$, —N($Z_2$)($Z_3$), —NH(O$Z_4$), —O—N=C($Z_5$)($Z_6$), —S(O)$_m$$Z_7$, —NH—$Z_8$ or —S—$Z_8$, or A is also an unsubstituted or $C_1$–$C_4$alkyl-substituted heterocyclic radical which has the free valence at a nitrogen atom, $Z_1$ is hydrogen, $C_1$–$C_{18}$alkyl, $C_3$–$C_{18}$alkyl which is interrupted by oxygen or >N—$Y_2$, $C_3$–$C_{18}$alkenyl, $C_5$–$C_8$-cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, $C_7$–$C_9$phenylalkyl, $C_7$–$C_9$phenylalkyl which is substituted at the phenyl ring by $C_1$–$C_4$alkyl; tetrahydrofurfuryl, tetrahydroabietyl, $C_1$–$C_{18}$alkanoyl, $C_3$–$C_{18}$alkenoyl, $C_3$–$C_{18}$alkanoyl which is interrupted by oxygen or >N—$Y_2$, $C_6$–$C_9$-cycloalkylcarbonyl, benzoyl, $C_1$–$C_4$alkyl-substituted benzoyl, thenoyl, furoyl or a group of formula IIa or IIb, $Z_2$ is hydrogen, $C_1$–$C_{18}$alkyl, OH-substituted $C_2$–$C_{18}$alkyl, $C_3$–$C_{18}$alkenyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl, $C_1$–$C_{18}$alkanoyl, $C_3$–$C_{18}$alkenoyl, $C_3$–$C_{18}$alkanoyl which is interrupted by oxygen or >N—$Y_2$, $C_6$–$C_9$cycloalkylcarbonyl, benzoyl, $C_1$–$C_4$alkyl-substituted benzoyl, thenoyl, furoyl, —$(CH_2)_p$COO—$X_2$ or a radical of formula IIb, $Z_3$ is hydrogen, $C_1$–$C_{18}$alkyl, OH-substituted $C_2$–$C_{18}$alkyl, $C_3$–$C_{18}$alkenyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or a group of formula IIb, or $Z_2$ and $Z_3$, taken together, are $C_3$–$C_6$alkylene, $C_3$–$C_6$oxoalkylene or $C_3$–$C_6$alkylene which is interrupted by oxygen or >N—$T_6$, $Z_4$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted penyl or $C_7$–$C_9$phenylalkyl, $Z_5$ and $Z_6$ are each independently of the other hydrogen, $C_1$–$C_{18}$alkyl, $C_2$–$C_{18}$alkenyl, $C_5$–$C_8$cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl or $C_7$–$C_9$phenylalkyl, or $Z_5$ and $Z_6$, together with the linking carbon atom, form an unsubstituted or $C_1$–$C_4$alkyl-substituted $C_5$–$C_8$cycloalkylidene ring, $Z_7$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or —$(CH_2)_r$COO—$Y_1$, $Z_8$ is unsubstituted or $C_1$–$C_4$alkyl-substituted 2-benzoxazolyl or unsubstituted or $C_1$–$C_4$alkyl-substituted 2-benzothiazolyl, $T_1$ and $T_2$ are each independently of the other hydrogen, $C_1$–$C_{18}$alkyl, $C_2$–$C_{18}$alkenyl, $C_5$–$C_8$cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl, $C_7$–$C_9$phenylalkyl or —$CH_2$—S—$X_1$, $T_3$ is hydrogen or $C_1$–$C_4$alkyl, $T_4$ is hydrogen, $C_1$–$C_{18}$alkyl, $C_2$–$C_{18}$alkenyl, $C_5$–$C_8$cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl, $C_7$–$C_9$phenylalkyl, —$CH_2$—S—$X_1$, —$(CH_2)_p$COO—$X_2$ or —$(CH_2)_q$O—$X_3$, $T_5$ is hydrogen, $C_1$–$C_4$alkyl, —OH, $C_6$–$C_{12}$alkoxy, $C_5$–$C_8$cycloalkoxy, allyl, benzyl or acetyl, $T_6$ is $C_1$–$C_{12}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl or $C_7$–$C_9$phenylalkyl, m is 1 or 2, w is 0 or 1, when n is 2, A is a group of formula IIIa, IIIb, IIIc, IIId, IIIe or IIIf, $G_1$ and $G_3$ are each independently of the other hydrogen, $C_1$–$C_{18}$alkyl, $C_3$–$C_{18}$alkenyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl, —$(CH_2)_p$COO—$X_2$ or a radical of formula IIb, $G_2$ is $C_2$–$C_{12}$alkylene, $C_4$–$C_{12}$alkylene which is interrupted by oxygen or >N—$Y_2$, $C_4$–$C_{12}$alkenylene, $C_4$–$C_{12}$alkynylene, ($C_1$–$C_4$alkylene)phenylene-($C_1$–$C_4$alkylene), a monocyclic saturated hydrocarbon radical having two free valences and containing 5 to 12 carbon atoms, phenylene, $C_1$–$C_4$alkyl-substituted phenylene or naphthylene, $C_2$–$C_{18}$alkanedioyl, $C_4$–$C_{18}$alkenedioyl or carboxybenzoyl, $G_4$ and $G_6$ are each independently of the other hydrogen, $C_1$–$C_{18}$alkyl, $C_3$–$C_{18}$alkenyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or a group of formula IIb, $G_5$ $C_2$–$C_{12}$alkylene, $C_4$–$C_{12}$alkylene which is interrupted by oxygen or >N—$Y_2$, $C_4$–$C_{12}$alkenylene, $C_4$–$C_{12}$alkynylene, ($C_1$–$C_4$alkylene)phenylene-($C_1$–$C_4$alkylene), a monocyclic saturated hydrocarbon radical having two free valences and containing 5 to 12 carbon atoms, phenylene, $C_1$–$C_4$alkyl-substituted phenylene or naphthylene, $G_7$ is $C_2$–$C_{12}$alkylene, $C_4$–$C_{12}$alkylene which is interrupted by oxygen or >N—$Y_2$, $C_4$–$C_{12}$alkenylene, $C_4$–$C_{12}$alkynylene, ($C_1$–$C_4$alkylene)phenylene-($C_1$–$C_4$alkylene), a monocyclic saturated hydrocarbon radical having two free valences and containing 5 to 12 carbon atoms, phenylene, $C_1$–$C_4$alkyl-substituted phenylene or naphthylene, $C_2$–$C_{18}$alkanedioyl, $C_4$–$C_{18}$alkenedioyl or carboxybenzoyl $G_8$ and $G_{10}$ are each independently of the other hydrogen, $C_1$–$C_{18}$alkyl, $C_3$–$C_{18}$alkenyl, $C_5$–$C_8$-cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or a group of formula IIb, $G_9$ and $G_{11}$ are $C_2$–$C_{12}$alkylene, $C_4$–$C_{12}$alkylene which is interrupted by oxygen or >N—$Y_2$, $C_4$–$C_{12}$alkenylene, $C_4$–$C_{12}$alkynylene, ($C_1$–$C_4$alkylene)phenylene-($C_1$–$C_4$alkylene), a monocyclic saturated hydrocarbon radical having two free valences and containing 5 to 12 carbon atoms, phenylene, $C_1$–$C_4$alkyl-substituted phenylene or naphthylene, $G_{12}$ is hydrogen, $C_1$–$C_{18}$alkyl, $C_3$–$C_{18}$alkenyl, $C_5$–$C_8$-cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or a group of formula IIb, and t is 1 or 2.

3. A compound according to claim 1, wherein the substituents $R_1$ are each independently of one another $C_1$–$C_{10}$alkyl, $C_2$–$C_{18}$alkenyl, $C_5$–$C_8$-cycloalkyl, $C_5$–$C_8$-cycloalkenyl, phenyl, $C_7$–$C_9$phenylalkyl or —$CH_2$—S—$X_1$, the substituents $R_2$ are each independently of one another hydrogen, $C_1$–$C_{10}$alkyl, $C_2$–$C_{18}$alkenyl, $C_5$–$C_8$cycloalkyl, $C_5$–$C_8$cycloalkenyl, phenyl, $C_7$–$C_9$phenylalkyl, —$CH_2$—S—$X_1$, —$(CH_2)_p$COO—$X_2$ or —$(CH_2)_q$O—$X_3$, the substituents $R_3$ are hydrogen, $R_4$ is hydrogen or $C_1$–$C_4$alkyl, $R_5$ is hydrogen, $C_1$–$C_4$alkyl or phenyl, $R_6$ is hydrogen, $C_1$–$C_4$alkyl or phenyl, $R_7$ is hydrogen or $C_1$–$C_4$alkyl, $R_8$ is hydrogen, $C_1$–$C_4$alkyl or phenyl, $X_1$ is $C_1$–$C_{10}$alkyl, $C_5$–$C_8$cycloalkyl, phenyl, $C_7$–$C_9$phenylalkyl or —$(CH_2)_r$COO—$Y_1$, $X_2$ is $C_1$–$C_{10}$alkyl, $C_5$–$C_8$cycloalkyl, phenyl or $C_7$–$C_9$phenylalkyl, $X_3$ is $C_1$–$C_{10}$alkyl, $C_5$–$C_8$cycloalkyl, phenyl, $C_7$–$C_9$phenylalkyl, $C_1$–$C_{10}$alkanoyl, $C_3$–$C_{18}$alkenoyl, $C_3$–$C_{18}$alkanoyl which is interrupted by oxygen; or benzoyl, $Y_1$ is $C_1$–$C_{10}$alkyl, $C_5$–$C_8$cycloalkyl, phenyl or $C_7$–$C_9$phenylalkyl, p is 0, 1 or 2, q is an integer from 0 to 8, r is 1 or 2, n is an integer from 1 to 4, and, when n is 1, A is a group —O—$Z_1$, —N($Z_2$)($Z_3$), —NH(O$Z_4$), —O—N=C($Z_5$)($Z_6$), —S(O)$_m$$Z_7$, —NH—$Z_8$ or —S—$Z_8$, or A is also an unsubstituted or $C_1$–$C_4$alkyl-substituted heterocyclic radical which has the free valence at a nitrogen atom, $Z_1$ is hydrogen, $C_1$–$C_{18}$alkyl, $C_3$–$C_{18}$alkyl which is interrupted by oxygen; $C_3$–$C_{18}$alkenyl, $C_5$–$C_8$cycloalkyl, $C_5$–$C_8$cycloalkenyl, $C_7$–$C_9$phenylalkyl, tetrahydrofurfuryl, $C_1$–$C_{10}$alkanoyl, $C_3$–$C_{18}$alkenoyl, $C_3$–$C_{18}$alkanoyl which is interrupted by oxygen; benzoyl or a group of formula IIa or IIb, $Z_2$ is hydrogen, $C_1$–$C_{18}$alkyl, OH-substituted $C_2$–$C_{10}$alkyl, $C_3$–$C_{18}$alkenyl, $C_5$–$C_8$cycloalkyl, phenyl, $C_7$–$C_9$phenylalkyl, $C_1$–$C_{10}$alkanoyl, $C_3$–$C_{18}$alkenoyl, $C_3$–$C_{18}$alkanoyl which is interrupted by oxygen; benzoyl, —$(CH_2)_p$COO—$X_2$ or a group of formula IIb, $Z_3$ is hydrogen, $C_1$–$C_{18}$alkyl, OH-substituted $C_2$–$C_{10}$alkyl, $C_3$–$C_{18}$alkenyl, $C_5$–$C_8$-cycloalkyl, phenyl, $C_7$–$C_9$phenylalkyl or a group of formula IIb, or $Z_2$ and $Z_3$, taken together, are $C_3$–$C_6$alkylene, $C_3$–$C_6$oxoalkylene or $C_3$–$C_6$alkylene which is interrupted by oxygen, $Z_4$ is $C_1$–$C_{10}$alkyl, $C_5$–$C_8$-cycloalkyl, phenyl or $C_7$–$C_9$phenylalkyl, $Z_5$ and $Z_6$ are each independently of the other hydrogen, $C_1$–$C_{10}$alkyl, $C_2$–$C_{18}$alkenyl, $C_5$–$C_8$cycloalkyl, $C_5$–$C_8$cycloalkenyl, phenyl or $C_7$–$C_9$phenylalkyl, or $Z_5$ and $Z_6$, together with the linking carbon atom, form a $C_5$–$C_8$cycloalkylidene ring, $Z_7$ is $C_1$–$C_{10}$alkyl, $C_5$–$C_8$cycloalkyl, phenyl, $C_7$–$C_9$phenylalkyl or —(CH$_2$)$_r$COO—Y$_1$, $Z_8$ is unsubstituted or $C_1$–$C_4$alkyl-substituted 2-benzoxazolyl or unsubstituted or $C_1$–$C_4$alkyl-substituted 2-benzothiazolyl, $T_1$ and $T_2$ are each independently of the other hydrogen, $C_1$–$C_{10}$alkyl, $C_2$–$C_{18}$alkenyl, $C_5$–$C_8$-cycloalkyl, $C_5$–$C_8$cycloalkenyl, phenyl, $C_7$–$C_9$phenylalkyl or —CH$_2$—S—X$_1$, $T_3$ is hydrogen or $C_1$–$C_4$alkyl, $T_4$ is hydrogen, $C_1$–$C_{10}$alkyl, $C_2$–$C_{18}$alkenyl, $C_5$–$C_8$cycloalkyl, $C_5$–$C_8$-cycloalkenyl, phenyl, $C_7$–$C_9$phenylalkyl, —CH$_2$—S—X$_1$, —(CH$_2$)$_p$COO—X$_2$ or —(CH$_2$)$_q$O—X$_3$, $T_5$ is hydrogen, $C_1$–$C_4$alkyl, —OH, $C_6$–$C_{12}$alkoxy, $C_5$–$C_8$cycloalkoxy, allyl, benzyl or acetyl, m is 1 or 2, w is 0 or 1, when n is 2, A is a group of formula IIIa, IIIb, IIIc, IIId, IIIe or IIIf, $G_1$ and $G_3$ are each independently of the other hydrogen, $C_1$–$C_{10}$alkyl, $C_3$–$C_{18}$alkenyl, $C_5$–$C_8$cycloalkyl, phenyl, $C_7$–$C_9$phenylalkyl, —(CH$_2$)$_p$COO—X$_2$ or a radical of formula IIb, $G_2$ is $C_2$–$C_{10}$alkylene, $C_4$–$C_{12}$alkylene which is interrupted by oxygen; $C_4$–$C_{10}$alkenylene, $C_4$–$C_{10}$alkynylene, ($C_1$–$C_4$alkylene)phenylene-($C_1$–$C_4$alkylene), a monocyclic saturated hydrocarbon radical having two free valences and containing 5 to 10 carbon atoms, phenylene, $C_2$–$C_{10}$alkanedioyl, $C_4$–$C_{10}$alkenedioyl or carboxybenzoyl, $G_4$ and $G_6$ are each independently of the other hydrogen, $C_1$–$C_{10}$alkyl, $C_3$–$C_{18}$alkenyl, $C_5$–$C_8$cycloalkyl, phenyl, $C_7$–$C_9$phenylalkyl or a group of formula IIb, $G_5$ is $C_2$–$C_{10}$alkylene, $C_4$–$C_{12}$alkylene which is interrupted by oxygen; $C_4$–$C_{10}$alkenylene, $C_4$–$C_{10}$alkynylene, ($C_1$–$C_4$alkylene)phenylene-($C_1$–$C_4$alkylene), a monocyclic saturated hydrocarbon radical having two free valences and containing 5 to 10 carbon atoms or phenylene, $G_7$ is $C_2$–$C_{10}$alkylene, $C_4$–$C_{12}$alkylene which is interrupted by oxygen; $C_4$–$C_{10}$alkenylene, $C_4$–$C_{10}$alkynylene, ($C_1$–$C_4$alkylene)phenylene-($C_1$–$C_4$alkylene), a monocyclic saturated hydrocarbon radical having two free valences and containing 5 to 10 carbon atoms, phenylene, $C_2$–$C_{10}$alkanedioyl, $C_4$–$C_{10}$alkenedioyl or carboxybenzoyl, $G_8$ and $G_{10}$ are each independently of the other hydrogen, $C_1$–$C_{10}$alkyl, $C_3$–$C_{18}$alkenyl, $C_5$–$C_8$cycloalkyl, phenyl, $C_7$–$C_9$phenylalkyl or a group of formula IIb, $G_9$ and $G_{11}$ are $C_2$–$C_{10}$alkylene, $C_4$–$C_{12}$alkylene which is interrupted by oxygen; $C_4$–$C_{10}$alkenylene, $C_4$–$C_{10}$alkynylene, ($C_1$–$C_4$alkylene)phenylene-($C_1$–$C_4$alkylene), a monocyclic saturated hydrocarbon radical having two free valences and containing 5 to 10 carbon atoms or phenylene, $G_{12}$ is hydrogen, $C_1$–$C_{10}$alkyl, $C_3$–$C_{18}$alkenyl, $C_5$–$C_8$cycloalkyl, phenyl, $C_7$–$C_9$phenylalkyl or a group of formula IIb, and t is 1 or 2.

4. A compound according to claim 1, wherein $R_5$, $R_6$, $R_7$ and $R_8$ are hydrogen.

5. A compound according to claim 1, wherein n is 1 or 2.

6. A compound according to claim 1, wherein n is 1,

A is a group of formula —N($Z_2$)($Z_3$), $Z_2$ is hydrogen, and $Z_3$ is hydrogen, $C_1$–$C_{25}$alkyl, OH-substituted $C_2$–$C_{25}$alkyl, $C_3$–$C_{24}$alkenyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl or a group of formula IIb.

7. A compound according to claim 1, wherein n is 1,

A is a group of formula —O—$Z_1$, and $Z_1$ is $C_1$–$C_{25}$alkyl which is interrupted by oxygen; or a group of formula IIa, and w is 1.

8. A compound according to claim 1, wherein the substituents $R_1$ are identical and are $C_1$–$C_5$alkyl or $C_5$–$C_8$cycloalkyl, the substituents $R_2$ are identical and are $C_1$–$C_5$alkyl, the substituents $R_3$ are hydrogen, and $R_4$ is hydrogen or $C_1$–$C_4$alkyl.

9. A compound according to claim 1, wherein the substituents $R_1$ are identical and are $C_1$–$C_5$alkyl or $C_5$–$C_8$cycloalkyl, the substituents $R_2$ are identical and are $C_1$–$C_5$alkyl, the substituents $R_3$ are hydrogen, $R_4$ is hydrogen or $C_1$–$C_4$alkyl, $R_5$, $R_6$, $R_7$ and $R_8$ are hydrogen, n is 1 or 2, and, when n is 1, A is a group —O—$Z_1$, —N($Z_2$)($Z_3$), —NH(O$Z_4$), —O—N=C($Z_5$)($Z_6$), —S(O)$_m$$Z_7$, —NH—$Z_8$ or —S—$Z_8$, or A is also an unsubstituted or $C_1$–$C_4$alkyl-substituted heterocyclic radical which has the free valence at a nitrogen atom, $Z_1$ is $C_1$–$C_{18}$alkyl, $C_3$–$C_{10}$alkyl which is interrupted by oxygen; $C_5$–$C_8$cycloalkyl, tetrahydrofurfuryl or a group of formula IIa or IIb, $Z_2$ is $C_1$–$C_{18}$alkyl, —OH-substituted $C_{2-4}$alkyl, $C_7$–$C_9$phenylalkyl, —(CH$_2$)$_p$COO—X$_2$ or a radical of formula IIb, $Z_3$ is hydrogen, $C_1$–$C_{18}$alkyl, —OH-substituted $C_{2-4}$alkyl, $C_7$–$C_9$phenylalkyl or a radical of formula IIb, or $Z_2$ and $Z_3$, taken together, are $C_3$–$C_6$oxoalkylene or $C_3$–$C_6$alkylene which is interrupted by oxygen, $Z_4$ is $C_7$–$C_9$phenylalkyl, $Z_5$ and $Z_6$, together with the linking carbon atom, form a $C_5$–$C_8$cycloalkylidene ring, $Z_7$ is $C_1$–$C_{10}$alkyl, $Z_8$ is unsubstituted or $C_1$–$C_4$alkyl-substituted 2-benzoxazolyl or unsubstituted or $C_1$–$C_4$alkyl-substituted 2-benzothiazolyl, $T_1$, $T_2$, $T_3$ and $T_4$ are each independently of the other hydrogen or $C_1$–$C_4$alkyl, $T_5$ is hydrogen or $C_1$–$C_4$alkyl, $X_2$ is $C_1$–$C_{10}$alkyl, m is 1 or 2, p is 1, w is 0 or 1, and when n is 2, A is a group of formula IIIa, IIIc or IIIf, $G_1$ and $G_3$ are each independently of the other hydrogen, $C_7$–$C_9$phenylalkyl or a radical of formula IIb, $G_2$ is $C_2$–$C_8$alkylene or a monocyclic saturated hydrocarbon radical with two free valences and containing 10 carbon atoms, $G_7$ is $C_2$–$C_8$alkylene or $C_4$–$C_{12}$alkylene which is interrupted by oxygen, and $G_{12}$ is $C_7$–$C_9$phenylalkyl or a group of formula IIb.

10. A composition comprising an organic material susceptible to oxidative, thermal, or light-induced degradation, and at least one compound of formula I as claimed in claim 1.

11. A composition according to claim 10, wherein the organic material is a synthetic polymer.

12. A composition according to claim 10, wherein the organic material is a polyolefin.

13. A composition according to claim 10, wherein the organic material is a solution-polymerised polybutadiene rubber.

14. A composition according to claim 10, wherein the organic material is a solution-polymerised styrene-butadiene copolymer or styrene-butadiene block copolymer.

15. A composition according to claim 10, wherein the organic material is an acrylonitrile-butadiene-styrene.

16. A method for stabilising an organic material against oxidative, thermal or light-induced degradation, which comprises incorporating into said organic material at least one compound of the formula I according to claim 1.

* * * * *